US011832801B2

(12) United States Patent
Katchman et al.

(10) Patent No.: US 11,832,801 B2
(45) Date of Patent: Dec. 5, 2023

(54) SWEAT AS A BIOFLUID FOR ANALYSIS AND DISEASE IDENTIFICATION

(71) Applicant: cARIZONA BOARD OF REGENTS ON BEHALF OF ARIZONA STATE UNIVERSITY, Scottsdale, AZ (US)

(72) Inventors: Benjamin Katchman, Tempe, AZ (US); Karen Anderson, Scottsdale, AZ (US); Jennifer Blain Christen, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 520 days.

(21) Appl. No.: 16/317,326

(22) PCT Filed: Jul. 11, 2017

(86) PCT No.: PCT/US2017/041551
§ 371 (c)(1),
(2) Date: Jan. 11, 2019

(87) PCT Pub. No.: WO2018/013579
PCT Pub. Date: Jan. 18, 2018

(65) Prior Publication Data
US 2019/0290248 A1 Sep. 26, 2019

Related U.S. Application Data

(60) Provisional application No. 62/360,787, filed on Jul. 11, 2016.

(51) Int. Cl.
*A61B 10/00* (2006.01)
*G01N 33/569* (2006.01)
*G01N 21/17* (2006.01)

(52) U.S. Cl.
CPC ... *A61B 10/0064* (2013.01); *G01N 33/56994* (2013.01); *G01N 21/17* (2013.01); *G01N 2333/05* (2013.01); *G01N 2333/11* (2013.01); *G01N 2469/20* (2013.01)

(58) Field of Classification Search
CPC ......... A61B 10/0064; G01N 33/56994; G01N 21/17; G01N 2333/05; G01N 2333/11; G01N 2469/20
See application file for complete search history.

(56) References Cited

U.S. PATENT DOCUMENTS

| 4,366,241 A | 12/1982 | Tom |
| 4,376,110 A | 3/1983 | David |
| 4,517,288 A | 5/1985 | Giegel |
| 4,542,751 A | 9/1985 | Webster |
| 4,837,168 A | 6/1989 | De Jaeger |
| 5,438,984 A | 8/1995 | Schoendorfer |
| 5,441,048 A * | 8/1995 | Schoendorfer ........ A61B 5/415 600/362 |
| 5,676,144 A | 10/1997 | Schoendorfer |
| 5,891,649 A | 4/1999 | Kidwell |
| 6,443,892 B1 | 9/2002 | Kidwell |
| 6,585,646 B2 | 7/2003 | Berlin |
| 8,956,859 B1 * | 2/2015 | Bermudes .......... G01N 33/6854 436/514 |
| 9,857,374 B2 | 1/2018 | LaBaer |
| 2002/0115921 A1 | 8/2002 | Berlin |
| 2003/0199743 A1 | 10/2003 | Berlin |
| 2003/0211550 A1 | 11/2003 | Johann |
| 2005/0106713 A1 * | 5/2005 | Phan .................. A61B 5/14514 702/19 |
| 2010/0130843 A1 * | 5/2010 | Caceres Galvez .......................... G01N 33/48792 600/346 |
| 2012/0283529 A1 * | 11/2012 | Marchand .......... G01N 33/5088 600/314 |
| 2012/0316079 A1 | 12/2012 | Rowlen |
| 2013/0183243 A1 * | 7/2013 | LaBelle ............. G01N 33/5438 424/9.1 |
| 2014/0025000 A1 * | 1/2014 | Currie ................ A61B 5/14546 604/66 |
| 2014/0275862 A1 * | 9/2014 | Kennedy .............. A61B 5/4266 600/307 |
| 2015/0005188 A1 * | 1/2015 | Levner ................ C12Q 1/6816 506/9 |
| 2015/0072338 A1 * | 3/2015 | Holmes .................. C12Q 1/706 435/5 |

(Continued)

FOREIGN PATENT DOCUMENTS

| WO | 2010/045247 A1 | 4/2010 |
| WO | 2012021887 A2 | 2/2012 |

(Continued)

OTHER PUBLICATIONS

Adewole OO, Erhabor GE, Adewole TO, Ojo AO, Oshokoya H, Wolfe LM, Prenni JE. Proteomic profiling of eccrine sweat reveals its potential as a diagnostic biofluid for active tuberculosis. Proteomics Clin Appl. May 2016; 10(5):547-53. doi: 10.1002/prca.201500071. Epub Apr. 1, 2016. (Year: 2016).*
Katchman BA, Zhu M, Blain Christen J, Anderson KS. Eccrine Sweat as a Biofluid for Profiling Immune Biomarkers. Proteomics Clin Appl. Nov. 2018;12(6):e1800010. doi: 10.1002/prca.201800010. Epub Jun. 28, 2018. (Year: 2018).*
Jadoon S, Karim S, Akram MR, Kalsoom Khan A, Zia MA, Siddiqi AR, Murtaza G. Recent developments in sweat analysis and its applications. Int J Anal Chem. 2015;2015:164974. doi: 10.1155/2015/164974. Epub Mar. 9, 2015. (Year: 2015).*
Brodersen M, Wirth M. Detection of HBsAg and HBsAb in sweat. Acta Hepatogastroenterol (Stuttg). Jun. 1976;23(3):194-201. (Year: 1976; Abstract Only).*
Sato K, Kang WH, Saga K, Sato KT. Biology of sweat glands and their disorders. I. Normal sweat gland function. J Am Acad Dermatol. Apr. 1989;20(4):537-63. (Year: 1989).*

(Continued)

*Primary Examiner* — Rachel B Gill
(74) *Attorney, Agent, or Firm* — Quarles & Brady LLP

(57) ABSTRACT

Provided herein are methods of detecting and measuring disease-associated analytes such as proteins and antibodies in a sweat sample. Also provided are methods of determining and monitoring the disease state or physiological condition of a subject using small sweat samples.

18 Claims, 8 Drawing Sheets

(56) References Cited

U.S. PATENT DOCUMENTS

| | | | |
|---|---|---|---|
| 2015/0362497 A1 | 12/2015 | Anderson | |
| 2016/0007893 A1* | 1/2016 | Roberts | A61B 5/0031 |
| | | | 600/309 |
| 2016/0058323 A1 | 3/2016 | Theranos | |
| 2016/0146754 A1* | 5/2016 | Prasad | A61B 5/1468 |
| | | | 204/547 |
| 2017/0045515 A1 | 2/2017 | Anderson | |
| 2017/0059563 A1 | 3/2017 | Smith | |
| 2017/0095184 A1* | 4/2017 | Heikenfeld | A61B 5/14546 |
| 2017/0122853 A1* | 5/2017 | Kobayashi | A61P 35/00 |
| 2017/0176423 A1 | 6/2017 | Anderson | |
| 2017/0177788 A1 | 6/2017 | Anderson | |
| 2017/0205409 A1 | 7/2017 | Anderson | |
| 2017/0327911 A1* | 11/2017 | Peters | C12Q 1/701 |
| 2017/0363631 A1 | 12/2017 | LaBaer | |
| 2017/0370836 A1* | 12/2017 | Gerion | G01N 21/82 |
| 2018/0160951 A1* | 6/2018 | Heikenfeld | A61B 5/01 |
| 2018/0172681 A1 | 6/2018 | Katchman | |
| 2018/0263539 A1* | 9/2018 | Javey | A61B 5/1477 |
| 2018/0320230 A1 | 11/2018 | LaBaer | |
| 2018/0353748 A1* | 12/2018 | Heikenfeld | A61B 5/14546 |
| 2019/0183394 A1* | 6/2019 | Beech | G01N 33/543 |
| 2019/0231236 A1* | 8/2019 | Heikenfeld | C12Q 1/006 |
| 2019/0250153 A1* | 8/2019 | Muthukumar | C12Q 1/68 |
| 2019/0302122 A1 | 10/2019 | Katchman | |
| 2020/0138347 A1* | 5/2020 | Heikenfeld | A61B 5/14546 |
| 2020/0155046 A1* | 5/2020 | Beech | A61B 5/0053 |
| 2021/0287798 A1* | 9/2021 | Peterson | A61B 5/0035 |
| 2021/0325380 A1* | 10/2021 | Muthukumar | G01N 33/521 |

FOREIGN PATENT DOCUMENTS

| | | | |
|---|---|---|---|
| WO | 2014120902 A1 | 8/2014 | |
| WO | 2015148202 A1 | 10/2015 | |
| WO | 2015148216 A1 | 10/2015 | |
| WO | 2015148273 A2 | 10/2015 | |
| WO | 2015/168515 A1 | 11/2015 | |
| WO | 2015167678 A1 | 11/2015 | |
| WO | 2015168515 A1 | 11/2015 | |
| WO | WO-2016028316 A1 * | 2/2016 | C12N 15/1093 |
| WO | 2016094558 A1 | 6/2016 | |
| WO | WO-2016105548 A1 * | 6/2016 | G01N 21/253 |
| WO | 2016195918 A1 | 12/2016 | |
| WO | 2017075141 A1 | 5/2017 | |
| WO | 2018013531 A1 | 1/2018 | |
| WO | WO-2018026931 A1 * | 2/2018 | A61B 5/14507 |
| WO | 2019099723 A2 | 5/2019 | |

OTHER PUBLICATIONS

Brodersen M, Wirth M. Detection of HBsAg and HBsAb in sweat. Acta Hepatogastroenterol (Stuttg). Jun. 1976;23(3):194-201. (Year: 1976).*

Peterson RA, Gueniche A, Adam de Beaumais S, Breton L, Dalko-Csiba M, Packer NH. Sweating the small stuff: Glycoproteins in human sweat and their unexplored potential for microbial adhesion. Glycobiology. Mar. 2016;26(3):218-29. Epub Nov. 17, 2015. (Year: 2015).*

Metze D, Jurecka W, Gebhart W, Schmidt J, Mainitz M, Niebauer G. Immunohistochemical demonstration of immunoglobulin A in human sebaceous and sweat glands. J Invest Dermatol. Jan. 1989;92(1):13-7. (Year: 1989).*

Okada T, Konishi H, Ito M, Nagura H, Asai J. Identification of secretory immunoglobulin A in human sweat and sweat glands. J Invest Dermatol. May 1988;90(5):648-51. (Year: 1988).*

Potter EV, Vincente JB, Mayon-WHite RT, Shaughnessy MA, Poon-King T, Earle DP. Skin infections and immunoglobulin A in serum, sweat, and saliva of patients recovered from poststreptococcal acute glomerulonephritis or acute rheumatic fever and their siblings. Am J Epidemiol. Jun. 1982; 115(6):951-9. (Year: 1982).*

Jadoon S, Karim S, Akram MR, Kalsoom Khan A, Zia MA, Siddiqi AR, Murtaza G. Recent developments in sweat analysis and its applications. Int J Anal Chem. 2015;2015:164974. Epub Mar. 9, 2015. (Year: 2015).*

Sagawa K, Kimura A, Saito Y, Inoue H, Yasuda S, Nosaka M, Tsuji T. Production and characterization of a monoclonal antibody for sweat-specific protein and its application for sweat identification. Int J Legal Med. Apr. 2003;117(2):90-5. Epub Oct. 3, 2002. (Year: 2002).*

The International Search Report and Written Opinion for International Patent Application No. PCT/US2017/041551 dated Jul. 11, 2017.

Smith, JT et al., Application of Flexible OLED Display Technology to Point-of-Care Medical Diagnostic Testing, Journal of Display Technology, Jan. 2015, vol. 12, No. 3; pp. 273-280; DOI: 1109/JDT.2015.2479457.

Accurso, F. J., et al. "Sweat chloride as a biomarker of CFTR activity: proof of concept and ivacaftor clinical trial data." Journal of Cystic Fibrosis 13.2 (2014): 139-147.

Anderson, N. L., et al. "Mass spectrometric quantitation of peptides and proteins using Stable Isotope Standards and Capture by Anti-Peptide Antibodies (SISCAPA)." Journal of proteome research 3.2 (2004): 235-244.

Brisson, G. R., et al. "A simple and disposable sweat collector." European journal of applied physiology and occupational physiology 63.3-4 (1991): 269-272.

Coghill AE, et al. Epstein-Barr virus antibodies and the risk of associated malignancies: review of the literature. American journal of epidemiology. 2014;180(7):687-95. doi: 10.1093/aje/kwu176. PubMed PMID: 25167864; PubMed Central PMCID: PMC4271109.

Engvall, E. "[28] Enzyme immunoassay ELISA and EMIT." Methods in enzymology. vol. 70. Academic Press, 1980. 419-439.

Jadoon S, et al. Recent developments in sweat analysis and its applications. International journal of analytical chemistry. 2015;2015:164974. doi: 10.1155/2015/164974. PubMed PMID: 25838824; PubMed Central PMCID: PMC4369929.

Komissarov A, et al. Rapid spread of influenza A(H1N1)pdm09 viruses with a new set of specific mutations in the Internal genes in the beginning of 2015/2016 epidemic season in Moscow and Saint-Petersburg (Russian Federation). Influenza and other respiratory viruses. 2016. doi: 10.1111/irv.12389. PubMed PMID: 26992820.

Petrie JG, et al. Persistence of Antibodies to Influenza Hemagglutinin and Neuraminidase Following One or Two Years of Influenza Vaccination. The Journal of infectious diseases. 2015;212(12):1914-22. doi: 10.1093/infdis/jiv313. PubMed PMID: 26014800; PubMed Central PMCID: PMC4655854.

Sarma, "Active Matrix OLED Using 150C a—Si TFT Backplane Built on Flexible Plastic Substrate," SPIE Symp. on Aerospace/Defense Sensing, vol. 5080, p. 180, 2003.

Sato K, et al. Biology of sweat glands and their disorders. I. Normal sweat gland function. Journal of the American Academy of Dermatology. 1989;20(4):537-63. PubMed PMID: 2654204.

Sato K, et al. Biology of sweat glands and their disorders. II. Disorders of sweat gland function. Journal of the American Academy of Dermatology. 1989;20(5 Pt 1):713-26. PubMed PMID: 2654213.

Wong J, et al. Rapid detection of antibodies in sera using multiplexed self-assembling bead arrays. Journal of Immunological methods. 2009;350(1-2):171-82. doi: 10.1016/j.jim.2009.08.013. PubMed PMID: 19732778; PubMed Central PMCID: PMC2974181.

European Patent Office. Extended European Search Report for application 17828316.4, dated Feb. 14, 2020.

Gao, W, et al. "Fully integrated wearable sensor arrays for multiplexed in situ perspiration analysis." Nature 529.7587 (2016): 509-514.

Cizza, G. et al: "Elevated Neuroimmune Biomarkers in Sweat Patches and Plasma of Premenopausal Women with Major Depressive Disorder in Remission: The Power Study", Biological Psychiatry, Elsevier Science, New York, NY; US, vol. 64, No. 10, Nov. 15, 2008 (Nov. 15, 2008), pp. 907-911.

* cited by examiner

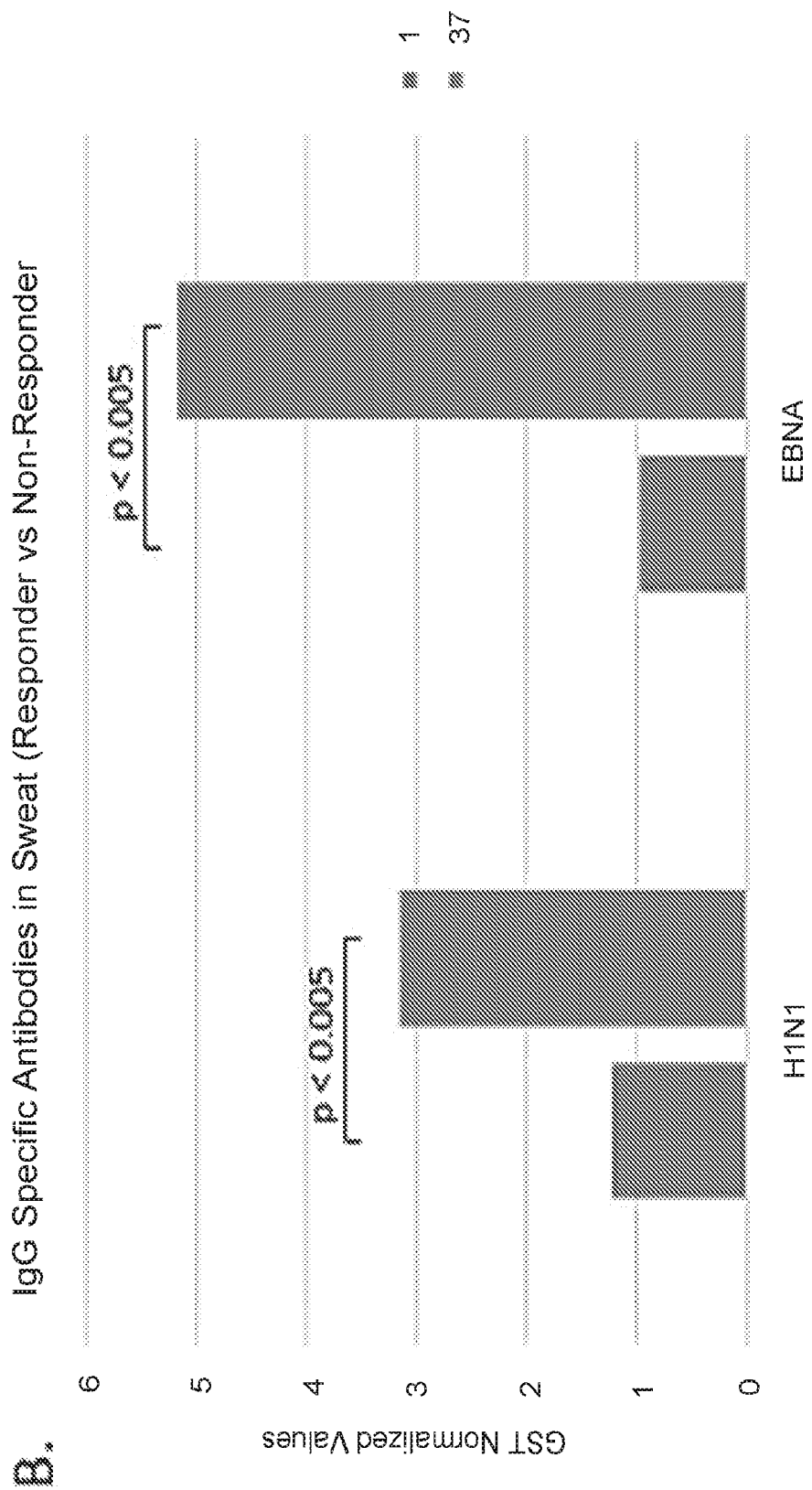
FIGS. 3A-3B, CONTINUED

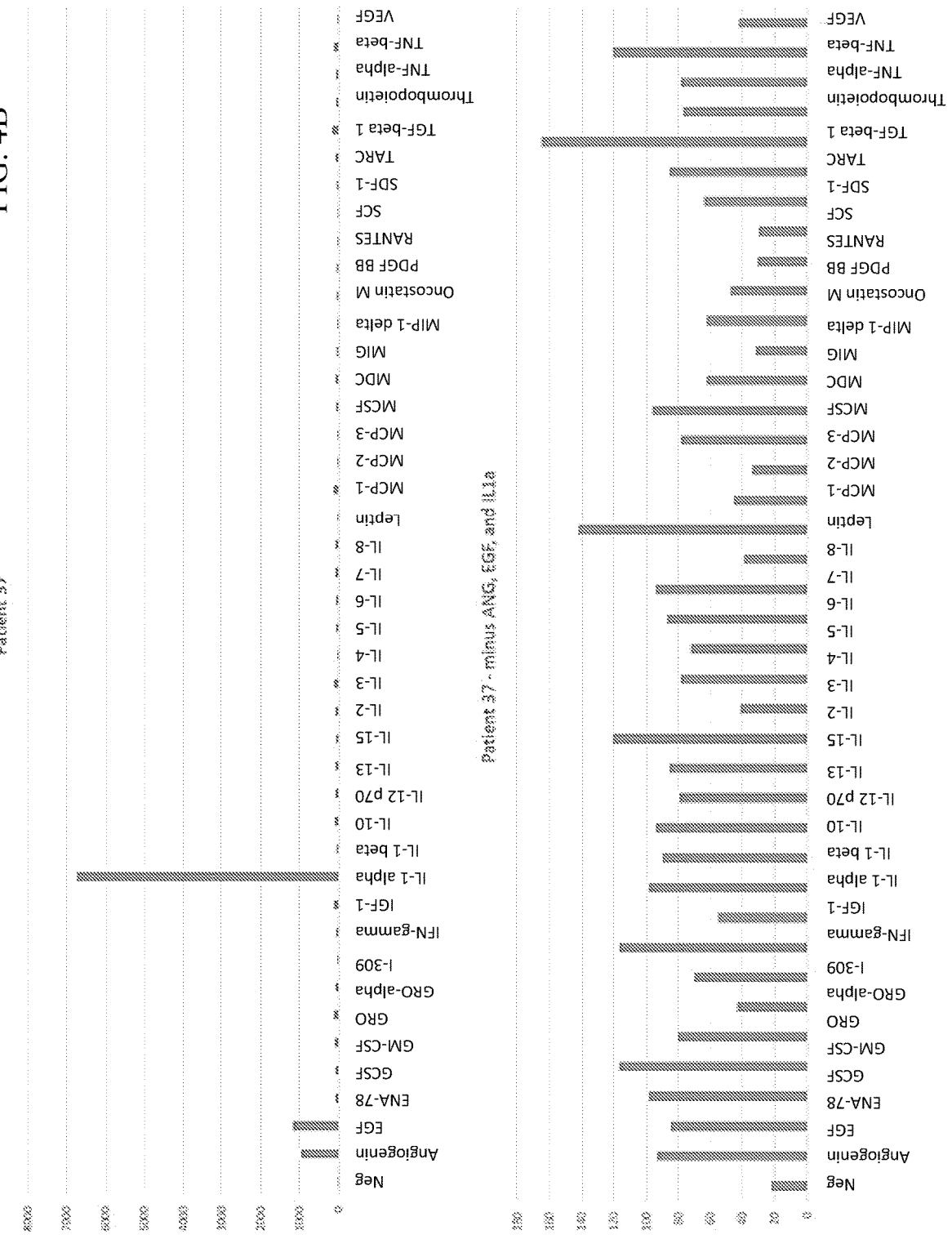

SWEAT AS A BIOFLUID FOR ANALYSIS AND DISEASE IDENTIFICATION

CROSS-REFERENCE TO RELATED APPLICATIONS

This application represents the national stage entry of PCT International Application No. PCT/US2017/041551, filed on Jul. 11, 2017, and claims the benefit of U.S. Provisional Application No. 62/360,787, filed on Jul. 11, 2016, which is hereby incorporated by reference as if set forth in its entirety for all purposes.

STATEMENT REGARDING FEDERALLY SPONSORED RESEARCH

This invention was made with government support under 1521904 awarded by the National Science Foundation. The government has certain rights in the invention.

BACKGROUND

Sweat is a clear, hypotonic biofluid produced by eccrine and apocrine glands located in the epidermis. Sweat is slightly acidic (pH range 4-6) and is composed mainly of water (99%), containing electrolytes (e.g., sodium, chloride, and potassium ions), urea, pyruvate, and lactate, but also proteins, peptides, amines, amino acids, and metal ions. Present in smaller concentrations are antigens, antibodies, and a variety of substances that are foreign to the body ("xenobiotics") such as drugs, cosmetics, and ethanol. These substances are stored in sweat glands, secreted into the sweat, and transported to the epidermis with partial reabsorption of sodium and chloride during transportation. Diseases can change sweat composition either by altering the concentration of common components or reporting new components that, in any case, could act as biomarkers of the given disease.

The analysis of eccrine sweat for diagnosis of cystic fibrosis by measuring concentrations of the electrolytes (chloride, sodium, and potassium ions) has long been used in the clinics, as shown for example in U.S. Pat. No. 4,542,751. The analysis of apocrine sweat for diagnosis of various diseases by the use of patches and the measurement of concentrations of several electrolytes has been proposed, e.g., U.S. Published Patent Application 2003/0199743. However, to date, the analytical results obtained for sweat analysis were not found sufficiently reliable and reproducible for any clinical application apart from cystic fibrosis. Importantly, standard point-of-care diagnostic sweat assays lack the ability to detect and identify disease-specific antibodies, peptides, and proteins from a wearable collection device. Accordingly, there remains a need for improved procedures for analyzing specific proteins and antibodies in sweat samples to provide more accurate indications of the health condition of a person.

BRIEF SUMMARY

The present invention overcomes the aforementioned drawbacks by presenting methods and devices for analyte detection from small sweat samples in a portable, wearable device. The invention described herein is intended to function as a wearable fluorescence microscopy laboratory able to detect signals at diagnostically relevant levels.

In a first aspect, provided herein is a method for determining a concentration of an analyte in sweat, comprising the steps of: providing between about 1 μl and about 50 μl of a body fluid sample comprising sweat, wherein the sample is collected using a wearable sample collection device; contacting at least a portion of the collected sample to an analyte measurement device comprising an assay unit, wherein the assay unit is configured to detect a plurality of analytes and comprises reactants for detection of the plurality of analytes, and wherein the wearable sample collection device and the analyte measurement device comprise a single integrated device; allowing the collected body fluid sample to react with the reactants, whereby a detectable reaction product is produced if a target analyte is present in the sample; and detecting and measuring the reaction product, wherein the presence of detectable reaction product indicates the presence of the target analyte in the sample; and wherein the amount of detectable reaction product is related to the concentration of the target analyte in the sample. The target analyte can be an antibody selected from the group consisting of an Epstein Barr Virus nuclear antigen 1 (EBNA1)-specific IgG antibody, an EBNA1-specific IgA antibody, a H1N1 influenza HA-specific antibody, a H1N1 influenza NP-specific antibody, H3N2 influenza HA-specific antibody, and H3N2 influenza NP-specific antibody. The reactants comprise a capture probe that binds specifically to the target analyte, and wherein the presence of a detectable reaction product indicates the binding of the capture probe to the target analyte. The capture probe can comprise a detectable moiety. The assay unit can be configured to run an enzymatic assay yielding a colored product, is configured to run an immunoassay, or both. The reactants can be selected from the group of enzymes, substrates, colorimetric indicators, antibodies, and combinations thereof. The body fluid sample can consist essentially of sweat. The target analyte can be selected from the group comprising of the following: antibodies, metabolites, proteins, glycoproteins, lipids, glycolipids, proteolipids, hormones, cytokines, growth factors, biomarkers, virus particles, bacteria, fungi, drug compounds, synthetic organic compounds, volatile odorants, toxicants, and pollutants.

In another aspect, provided herein is a method of monitoring changes in an individual's health state over time, the method comprising (a) detecting the presence of one or more target analytes in a first sweat sample from the subject, wherein detecting comprises: (i) collecting about 5 μL to about 20 μL of a body fluid sample comprising sweat, wherein the sample is collected using a wearable sample collection device; (ii) contacting at least a portion of the collected sample to an analyte measurement device comprising an assay unit, wherein the assay unit is configured to detect a plurality of analytes and comprises reactants for detection of the plurality of analytes, and wherein the wearable sample collection device and the analyte measurement device comprise a single integrated device; (iii) allowing the collected body fluid sample to react with the reactants, whereby a detectable reaction product is produced if a target analyte is present in the sample; and (iv) detecting the reaction product, wherein the presence of detectable reaction product indicates the presence of the target analyte in the sample; (b) measuring a concentration of the detected target analyte of the first sweat sample to establish a baseline level of said target analyte, wherein the amount of detectable reaction product is related to the concentration of the target analyte in the sample; (c) repeating steps (a) and (b) to detect and measure the concentration of target analyte in a second sweat sample obtained from the individual at after a predetermined interval of time; (d) comparing the concentrations measured for the first and second sweat samples to detect a positive or negative change in the concentrations as an indicator of a positive or negative change in the individual's health state over the predetermined interval of time. The target analyte can be an antibody selected from the group consisting of an Epstein Barr Virus nuclear antigen 1 (EBNA1)-specific IgG antibody, an EBNA1-specific IgA antibody, a H1N1 influenza HA-specific antibody, a H1N1 influenza NP-specific antibody, H3N2 influenza HA-specific antibody, and H3N2 influenza NP-specific antibody. Each of the first and second sweat samples can consist essentially of sweat. The wearable collection device can be positioned at essentially the same location on the individual's body for each sample collection step. The reactants can comprise a capture probe that binds specifically to the target analyte, and wherein the presence of a detectable reaction product indicates the binding of the capture probe to the target analyte. The capture probe can comprise a detectable moiety. The assay unit can be configured to run an enzymatic assay yielding a colored product, is configured to run an immunoassay, or both. The reactants can be selected from the group of enzymes, substrates, colorimetric indicators, antibodies, and combinations thereof. The target analyte can be selected from the group comprising of the following: antibodies, metabolites, proteins, glycoproteins, lipids, glycolipids, proteolipids, hormones, cytokines, growth factors, biomarkers, virus particles, bacteria, fungi, drug compounds, synthetic organic compounds, volatile odorants, toxicants, and pollutants.

In another aspect, provided herein is a method of detecting a disease-specific antibody in a body fluid sample, the method comprising: collecting about 5 µL to about 20 µL of a body fluid sample comprising sweat, wherein the sample is collected using a wearable sample collection device; contacting at least a portion of the collected sample to an analyte measurement device comprising an assay unit, wherein the assay unit is configured to detect at least one disease-specific antibody and comprises reactants for detection of the at least one disease-specific antibody, and wherein the wearable sample collection device and the analyte measurement device comprise a single integrated device; allowing the collected body fluid sample to react with the reactants, whereby a detectable reaction product is produced if a target disease-specific antibody is present in the sample; and detecting and measuring the reaction product, wherein the presence of detectable reaction product indicates the presence of the target disease-specific antibody in the sample; and wherein the amount of detectable reaction product is related to the concentration of the target disease-specific antibody in the sample. The target disease specific antibody can be selected from the group consisting of an Epstein Barr Virus (EBV)-specific IgG antibody, an EBV-specific IgA antibody, a H1N1 influenza HA-specific antibody, a H1N1 influenza NP-specific antibody, H3N2 influenza HA-specific antibody, and H3N2 influenza NP-specific antibody. The amount of detectable reaction product can be compared to a standard. The method can further comprise employing the concentration determined in (d) to distinguish between healthy subjects and subjects having a target analyte-associated disease. The body fluid sample can consist essentially of sweat.

The foregoing and other advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF DRAWINGS

The invention is herein described, by way of example only, with reference to the accompanying drawings, wherein:

FIG. 1B is an enlarged view of the data below the 14000 pg/mL concentration shown in FIG. 1A.

FIGS. 4A-4B demonstrate identification of a broad range of cytokines secreted in sweat. Sweat samples were collected from two patients: patient 1 (FIG. 4A) and patient 37 (FIG 4B) prior to sustained exercise. Data are presented as normalized median signal values. For each patient, upper graphs display all 42 cytokines evaluated and represents the cytokines with the highest signals. The lower graphs for each patient represent the remaining cytokines to further demonstrate their detectable signal levels well above background.

Figure 1A:
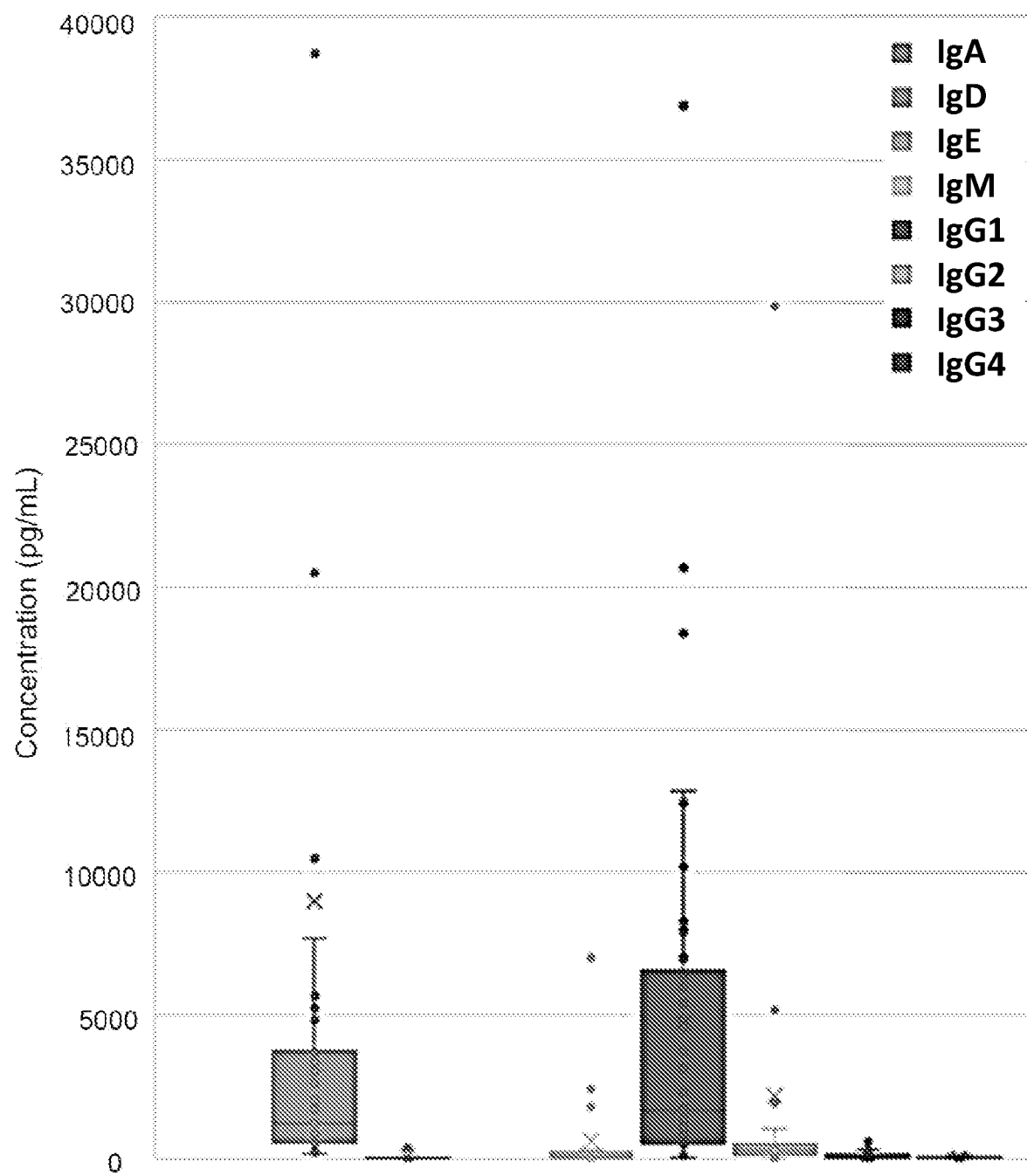
FIGS. 1A-1B demonstrate antibody isotypes present in sweat. Sweat was collected from 50 healthy individuals and analyzed for the presence of human antibody (Ig) isotypes. Data presented are average raw values of the 50 healthy individuals. There was wide variability in isotype expression among individuals although, IgG1 and IgA were present in every individual with little variation (FIG. 1A). Additional Ig isotypes were present at lower concentrations and with increased variability among the participants (FIG 1B).

It is to be understood that the foregoing drawings, and the description below, are provided primarily for purposes of facilitating understanding the conceptual aspects of the invention and possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DETAILED DESCRIPTION

Before the present invention is described in further detail, it is to be understood that the invention is not limited to the particular embodiments described. It is also to be understood that the terminology used herein is for the purpose of describing particular embodiments only, and is not intended to be limiting. The scope of the present invention will be limited only by the claims.

As used herein, the singular forms "a", "an", and "the" include plural embodiments unless the context clearly dictates otherwise.

Specific structures, devices, transistors, and methods relating to flexible wearable sweat analysis devices have been disclosed. It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements.

The methods provided herein are based at least in part on the inventors' discovery that it is possible to detect cytokines from small volumes of sweat collected using wearable sweat collection devices. Diseases can change sweat composition either by altering the concentration of common components or reporting new components that, in any case, could act as biomarkers of the given disease. Due to the presence of very nominal impurities, the sample preparation of sweat is very easy as compared with other biofluids. In addition, sweat samples are less prone to adulterations; thus such samples can be stored for long periods. Unlike other biofluids, sweat possesses excellent features including noninvasive sampling. This is critical in dealing with people such as hemophiliacs, neonates, or elderly individuals, blood sampling of whom is either difficult or dangerous, and for avoiding infections to patients who need daily analysis. The ability to detect fluctuations in analyte levels, including disease-associated cytokine or antibody levels, in small sweat samples has broad implications for disease diagnosis and monitoring.

Accordingly, provided herein are systems, devices, and methods for detecting an analyte in a sweat sample. In certain embodiments, the method comprises comprising the steps of: providing between about 1 µl and about 50 µl of a body fluid sample comprising sweat, wherein the sample is collected using a wearable sample collection device; contacting at least a portion of the provided sample to an analyte measurement device comprising an assay unit, wherein the assay unit is configured to detect a plurality of analytes and comprises reactants for detection of the plurality of analytes, and wherein the wearable sample collection device and the analyte measurement device comprise a single integrated device; allowing the collected body fluid sample to react with the reactants, whereby a detectable reaction product is produced if a target analyte is present in the sample; and detecting the presence of a reaction product which indicates the presence of the target analyte in the sample. The method can further comprise measuring the amount of detectable reaction product relative to a standard, wherein the amount is related to the concentration of the target analyte in the sample.

As used herein, the term "sweat" refers to the clear, hypotonic biofluid produced by eccrine and apocrine sweat glands, and the term "sweat sample" refers to sweat collected for analysis or a sample of body fluid that comprises a subject's sweat. Sweat samples can be taken from a subject at defined time intervals (e.g., hourly, daily, weekly, or monthly) or at any suitable time interval as would be performed by those skilled in the art. The term "subject" or "patient" as used herein typically denotes humans, but may also encompass reference to non-human animals, preferably warm-blooded animals, more preferably mammals, such as, e.g., non-human primates, rodents, canines, felines, equines, ovines, porcines, and the like. For the methods provided herein, small volumes of sweat are sufficient for detecting target analytes that are proteins, peptides, or antibodies. As described in the Example that follows, sweat volumes as small as about 1 microliters (µl) to about 10 µl can be used to specifically detect cytokines and disease-specific antibodies.

The target analyte can be any specific substance or component that one is desirous of detecting and/or measuring using chemical, physical, enzymatic, and/or optical analysis. In preferred embodiments, the target analyte is an antibody such as a disease-specific antibody. In some cases, the target analyte is an Epstein Barr Virus (EBV)-specific IgG antibody, an EBV-specific IgA antibody, a H1N1 influenza HA-specific antibody, a H1N1 influenza NP-specific antibody, H3N2 influenza HA-specific antibody, or H3N2 influenza NP-specific antibody. Other target analytes include, but are not limited to, other antibodies, cytokines, amino acids, peptides, polypeptides, enzyme substrates, or metabolites including those that indicate a particular metabolic state or disease state; other markers of disease states or conditions, drugs of abuse, therapeutic and/or pharmacologic agents, electrolytes, physiological analytes of interest (e.g., calcium, potassium, sodium, chloride, bicarbonate ($CO_2$), glucose, urea (blood urea nitrogen), lactate, hematocrit, and hemoglobin), lipids, and the like. In certain embodiments, the analyte is a physiological analyte of interest, for example glucose, or a chemical that has a physiological action, for example a drug or pharmacological agent. In preferred embodiments, one or more target analytes are selected from the group comprising antibodies, peptides, proteins, cytokines, and growth factors.

Preferably, the target analyte is a disease-associated protein or other biomolecule. In some cases, target analytes include, without limitation, IgG and IgA antibodies. In some cases, the target analyte is a disease-associated antibody. For example, target analytes can include IgG antibodies specific for Epstein-Barr Nuclear Antigen 1 (EBNA1), which is associated with latent infection by Epstein-Barr virus (EBV). Other disease-associated antibodies detectable according to the methods provided herein include IgG antibodies specific for influenza H1N1 NP as well as antibodies specific for influenza H3N2 HA and NP. Preferably, the target analyte is an antibody selected from the group consisting of an EBV-specific IgG antibody, an EBV-specific IgA antibody, a H1N1 influenza HA-specific antibody, a H1N1 influenza NP-specific antibody, H3N2 influenza HA-specific antibody, and H3N2 influenza NP-specific antibody.

Figure 4A:
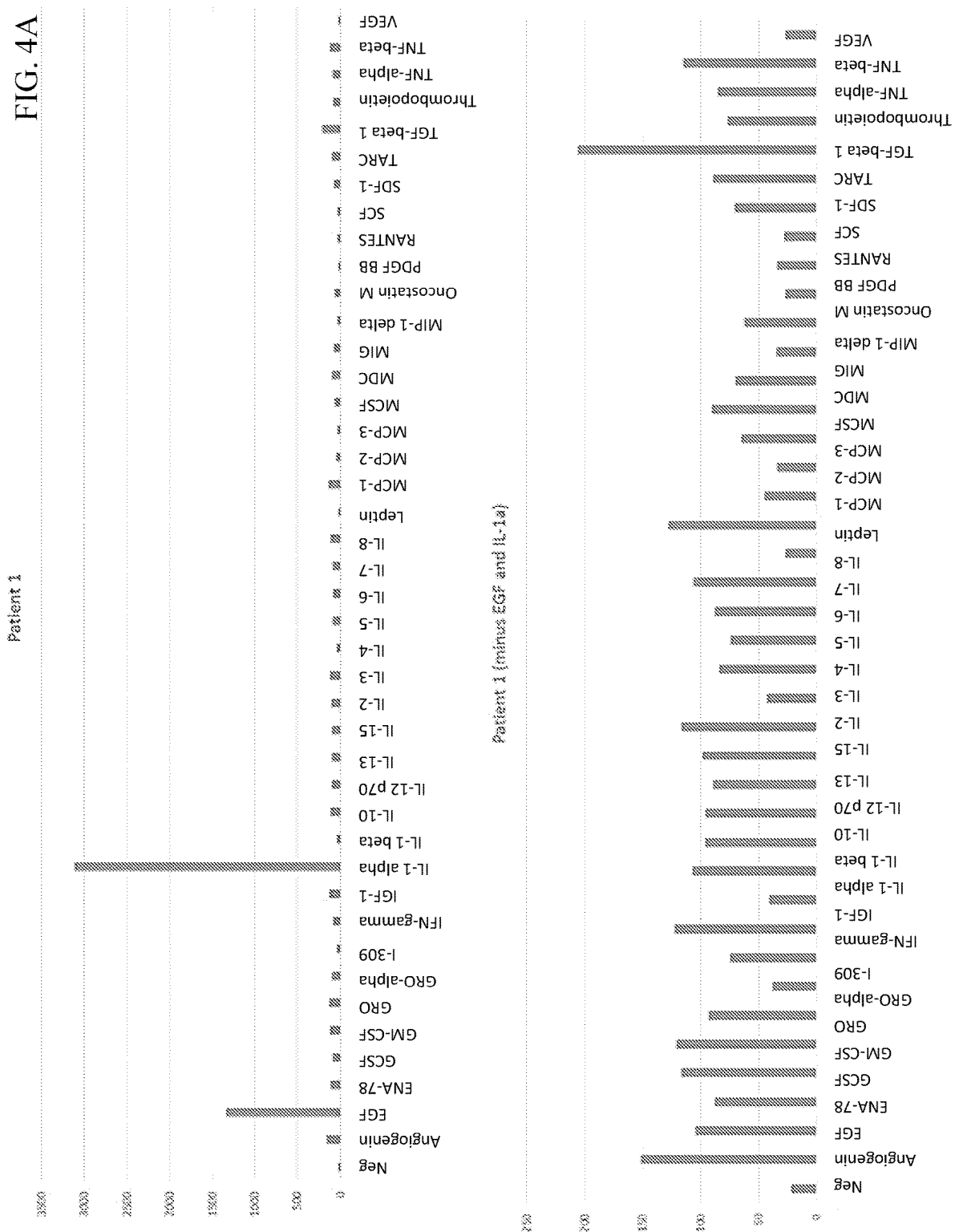

In other cases, target analytes include cytokines. As used herein, the term "cytokine" refers to a broad class of small proteins (~5-20 kDa) that are important in cell signaling, immunological responses to diseases, as well as indicating fatigue or stress. For example, cytokines that can be detected and measured according to the methods provided herein include, without limitation, IL-8 (CXCL8), GCSF, GM-CSF, GRO alpha/beta/gamma, IL-1 alpha (IL-1 F1), IL-2, IL-3, IL-5, IL-6, IL-7, IL-10, IL-13, IL-15, IFN-gamma, MCP-1 (CCL2), MCP-2 (CCL8), MCP-3 (MARC/CCL7), MIG (CXCL9), RANTES (CCL5), TGF beta 1, TNF alpha, TNF beta (TNFSF1B). Additional cytokines that can be detected and measured according to the methods provided herein include, without limitation, those set forth in FIGS. 4A-4B.

Other analytes that can be detected according to the methods provided herein include, without limitation, cancer markers (e.g., prostate-specific antigen (PSA), epidermal growth factor receptor (EGFR), cancer antigen CA 15-3), pathogens (e.g., *P. gingivalis, Chlamydia organisms, Streptococcus* organisms, viruses, organisms that cause common infectious diseases such as the flu, measles, etc., *Bacillus anthracis* and other organisms that may be used in biological warfare or terrorism, etc.), melatonin, insulin, aldosterone, testosterone, progesterone, andostenedione, estriol, estrone, growth factors (e.g., EGF, NGF, IGF-1), antibiotics (e.g., penicillin, tetracycline), vitamins, minerals, toxins, antioxidants, components of food products that are common allergens (e.g., peanuts and/or tree nuts), proteins and nucleic acids (e.g., DNA, RNA), including host and non-host (e.g., pathogenic) proteins and nucleic acids.

Preferably, the analyte measurement device comprises an assay unit configured to detect a plurality of analytes, and comprises reactants for detection of the plurality of analytes. As used herein, the terms "reactants," "reaction means," and "reaction agent" refer to compositions that provide for a reaction. In some cases, reactants create a detectable signal in the presence of an analyte. For example, reactants include, but are not limited to: enzymes, cofactors, and buffers for enzymatic reactions; ligands, analytes, or biosensors; and any other composition that facilitates a reaction. Reactants can include, without limitation, capture probes, enzymes, substrates, colorimetric indicators, antibodies, and combinations thereof. In some cases, reactants comprise a capture probe that binds specifically to the target analyte. In such cases, the presence of a detectable reaction product indicates the binding of the capture probe to the target analyte. In some cases, capture probes comprise a detectable moiety such as a fluorescent or luminescent moiety. In some preferred embodiments, the detectable signal comprises the formation of a color. In other preferred embodiments, the detectable signal comprises a change in color.

In some cases, the presence of target analytes in a sweat sample is detected by visible indicators, colorimetric indicators, chemical or monoclonal antibody detection techniques, electronic sensors, clinical laboratory analysis, or instrumental techniques. As used herein, the terms "detect" and "detection" refer to identifying the presence, absence, or amount of the object to be detected. Quantitative detection methods such as chemiluminescence immunoassays, enzyme immunoassays (EIA), radioimmunoassays, and fluorescence immunoassays, an ELISA methods are particularly sensitive and useful for the methods provided herein. Other detection methods useful for the methods provided herein include, for example, enzyme-linked immunosorbent assays (ELISA) (Engvall et al., *Methods in Enzymol.* 70:419-439 (1980)), SISCAPA (Stable Isotope Standards and Capture by Anti-Peptide Antibodies) (Anderson et al., *J Proteome Res.* 2004 March-April; 3(2):235-44), mass spectrometry, immunofluorescence assays, Western blot, affinity chromatography (affinity ligand bound to a solid phase), fluorescent antibody assays, immunochromatography, and in situ detection with labeled antibodies. See, e.g., U.S. Pat. Nos. 4,366,241; 4,376,110; 4,517,288; and 4,837,168).

Measurement of the concentration of a target analyte in a small sweat sample can be determined (for example, at the protein level or nucleic acid level) using any method(s) known in the art. A molecule or analyte (e.g., a polypeptide, peptide, antibody), or a group of two or more molecules or analytes, is "measured" in a sample when the presence or absence and/or quantity of said molecule or analyte or of said group of molecules or analytes is detected or determined in the sample, preferably substantially to the exclusion of other molecules and analytes. The terms "quantity", "amount" and "level" are synonymous and generally well-understood in the art. The terms as used herein may particularly refer to an absolute quantification of a molecule or an analyte in a sample, or to a relative quantification of a molecule or an analyte in a sample, i.e., relative to another value such as relative to a reference value as taught herein, or to a range of values indicating a base-line expression of the biomarker. These values or ranges can be obtained from a single patient or from a group of patients. In some cases, target analyte measurements are compared to a standard or set of standards.

In another aspect, a method is provided for measuring the concentration of an analyte present in a biological sample comprising sweat. The method can comprise detecting one or more target analytes in a biological sample comprising sweat from a subject. In some cases, the methods provided herein can be applied to sweat volumes between about 1 μl and about 50 μl (e.g., about 1, 2, 5, 10, 15, 20, 25, 30, 35, 40, 45, 50 μl). As described in the Example that follows, small sweat volumes can be used to specifically detect and measure target analytes including cytokines and disease-associated antigens.

Preferably, sweat is collected from a subject using a wearable sweat collection device. In some cases, the wearable sweat collection device is a disposable or reusable device configured to be placed and secured on the skin of a subject such that sweat collection can occur while the subject is sedentary or while active and moving around. The wearable sweat collection device can be configured for temporary or prolonged retention of a collected sweat sample. In some cases, the collection device comprises tubing, where an open end of the tubing is in contact with the skin, and the device is configured such that sweat flowing between the skin and the collection device is collected in the tubing. The tubing can be made of plastic or another flexible material. In some cases, the wearable sweat collector is a Macroduct Sweat Collector, where sweat flowing between the skin and the concave undersurface of the Macroduct collector is collected in a length of microbore tubing. In some cases, the Macroduct sweat collector is used as part of the Macroduct® Sweat Collection System (Wescor/ELITech Group, Logan, UT). The system utilizes pilocarpine iontophoresis for sweat gland stimulation and a spiral microbore tubing sweat collector monitored by a small amount of dye. Although there is considerable variation between patients, the average individual will produce approximately 60 μL of sweat during a 30-minute collection interval (E1). In some cases, sweat collection can be performed as described by Accurso et al., *J Cyst Fibros.* 2014 March; 13(2): 139-147.

In certain embodiments, the wearable sweat collection device is made of any appropriate type of flexible or stretchable material. Various kinds of devices based on an ultrathin and stretchable design have been developed for monitoring individual health status and, in some cases, delivering the corresponding feedback therapy. An alternative sweat collection device, comprising a collection capsule capable of being pierced or lanced by a needle to extract the collected sweat sample, is described by Brisson et al., *Eur. J Applied Physiol.* 63:269-72 (1991).

Figure 5:
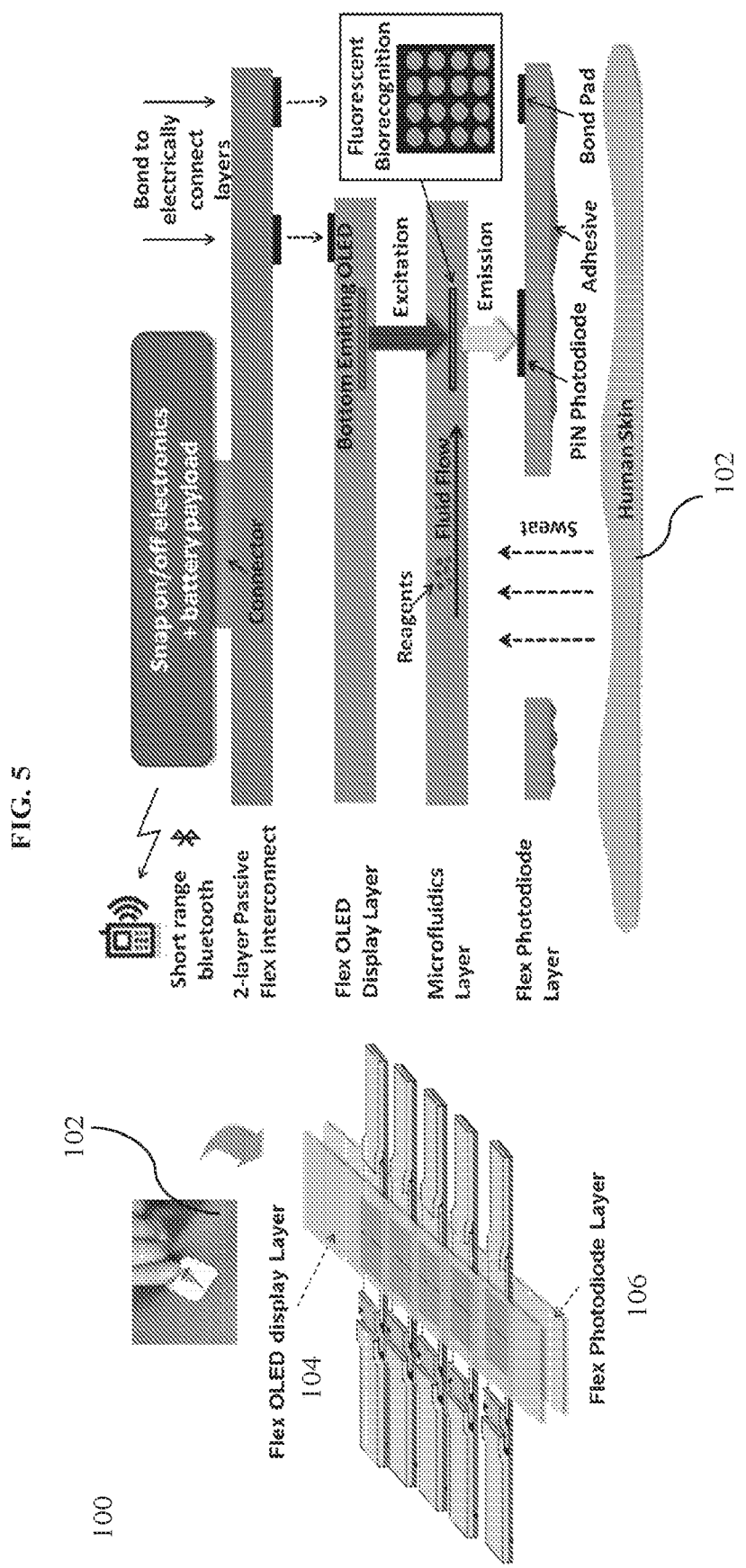
FIG. 5 provides a block diagram of an example wearable device. Device 100 comprises a lateral flow test strip sandwiched between an organic light emitting diode (OLED) or light emitting diode (LED) array 104 and a photodiode array 106 on a flexible substrate.

Preferably, the wearable sweat collection device and the analyte measurement device comprising an assay unit are integrated into a single device for direct measurement of one or more analytes in a collected sweat sample. Preferably, the integrated device is a wearable device configured to carry out the methods described herein to detect an analyte in a sweat sample collected from the person wearing the device. Referring to FIG. 5, a schematic of an example wearable biomedical device 100 implemented according to the present application is provided. Device 100 can be placed directly on the skin 102 of a subject. Because it is pliable, it conforms closely to the skin of the subject. The device can comprise a flexible display layer 104 comprising an organic light emitting diode (OLED) screen, a light emitting diode (LED) screen, liquid crystal display (LCD) screen, flexible OLED screen, or other suitable display systems, and further comprise an array of photodiodes. Preferably, flexible display layer 104 comprises a flexible two-dimensional array of LEDs or OLEDs and a flexible two-dimensional array of photodiodes 106 on a flexible substrate. An example photodiode is a PiN photodiode. Individual OLEDs can emit different colors of light.

Preferably, the flexible display layer can be thin-approximately the same thickness as a piece of paper- and a typically-transparent sheet of plastic. It can be constructed by sequentially layering and patterning nanoscale thin films. This approach allows the electronics functionality to be built or integrated directly into flexible plastic substrates using thin film components-such as an arrangement of one or more light emitting diodes (LEDs), OLEDs, PiN photodiodes, and thin film transistor (TFT) array technology-rather than separately bonding a large number of discrete electronic components. In TFT array technology, the typical flat panel display or PiN photodiode pixel is approximately 200 μm. Hence, an 8×8 array of 64 pixels using active matrix display technology is now less than 2 mm instead of one to two inches. This is now small enough to work with the limited sample volumes available and eliminate the need for separate fluid chambers.

Referring again to FIG. 5, in some cases, LED or OLED pixels in an array may be activated (turned on) sequentially to separately illuminate each of the separate reactants regions or spots in the combination microfluidic reaction and detection chamber. At the same time each of the OLED pixels is activated sequentially, opposing PiN photodiodes in a separate photodiode array will also be sequentially selected and the detected optical signal for each individual photodiode can be read out and recorded using, for example, a separate integrated circuit.

The flexible two-dimensional array of photodiodes may comprise a PiN photodiode pixel array. At the conceptual level, the PiN photodiode pixel array is essentially a digital camera. Light emitted by the fluorophore provides the illumination, and the photodiode array functions similarly to the solid state CMOS or CCD imager in a digital camera. However, unlike CCDs or CMOS imagers, which use silicon wafer semiconductor processing, a conventional PiN photodiode detector array is typically manufactured using thin film transistor (TFT) technology on large glass substrates—similar to the process used to manufacture large area flat panel liquid crystal displays (LCDs). To make the PiN photodiode detector array flexible, the substrate may comprise a polymer. In preferred embodiments, the substrate may comprise a 125 m thick, flexible, and extremely tough polyethylene naphthalate (PEN) plastic substrate from DuPont.

The light source may comprise organic light emitting diode (OLED) display technology. As shown in FIG. 5, an OLED display consists of an array of emissive light emitting elements, typically called pixels. The OLED pixel shown includes two thin film transistors (TFTs) and a capacitor, which are used to provide the ability to individually address (i.e., turn on) each OLED pixel in the array (K. R. Sarma, "Active Matrix OLED Using 150C a-Si TFT Backplane Built on Flexible Plastic Substrate," SPIE Symp. on Aerospace/Defense Sensing, vol. 580, p. 180, 2003). The thin OLED organic layer shown in FIG. 5 emits a bright light when a forward voltage bias is applied across the transparent anode and reflective cathode terminal, with the color of the emitted light as a function of the materials in the OLED organic layer, and the brightness a function of the current.

In some cases, a 4×4 photodiode array is employed in combination with a 4×4 OLED pixel array. This combination enables the detection of at least 16 different analytes (e.g., pathogens, disease biomarkers). It should be noted that a 4×4 pixel array is shown in FIG. 5 for convenience only and the arrays can have higher resolution. It should further be noted that the microfluidic system and the optical system are not drawn to scale in FIG. 5. In an actual device, the array size may more closely match the dimensions of the microfluidic detection chamber.

Referring again to FIG. 5, the assay unit is a microfluidic or nanofluidic layer comprising reactants such as, for example, one or more selective binding fluorescent labels and immobilized selective binding species. In certain embodiments, a collected sweat sample is brought into contact with a dried fluorescent labeled antibody in the microfluidics layer. The now fluorescently labeled sample can be captured by a second antibody immobilized on the surface of the detection chamber to complete the identification of the analyte(s) (e.g., biomarkers or pathogens) in the sweat sample. A downstream sample outlet wick, which can be as simple as a large and thick piece of blotter paper, may then be used to draw off any excess fluid as well as clear the detection chamber of un-reacted material. Sequentially illumination by each OLED pixel in the display layer can occur as the sample is contacted by reactants in the microfluidics layer, and the concentration of each antigen or antibody present in the sample may be proportional to the intensity of light emitted from the labeled antibody/antigen immunocomplex that is detected by the opposing PiN photodiode pixel.

In some cases, the wearable sweat collection device further comprises an iontophoresis interface to locally stimulate the skin to produce sweat. Iontophoresis process involves delivery of stimulating agonists to the sweat glands with the aid of an electrical current. For example, the device can include an electrode and a unit that produces a low electric current to elicit local absorption of a sweat gland secretory stimulating compound such as pilocarpine. Advantageously, the inclusion of an iontophoresis interface permit on-demand sweat collection and analysis for inactive subjects.

In some cases, the assay unit of an analyte measurement device comprises an electrode coated with capture probes having specificity for a particular target analyte. Capture probes coating the electrode would specifically bind the target analyte. As target analyte bind to capture probes on the electrode, target analyte-capture probe complexes should act as a barrier to electrical current, increasing the electrical impedance in a measurable way. Therefore, detecting can further comprise contacting a capture probe-coated electrode to a collected sweat sample, applying an alternating electrical current to the electrode, detecting a change in electrical impedance as an indicator that the target analyte is present in the sweat sample.

In another aspect, provided herein is a method for monitoring changes in an individual's health state over time. In some cases, the method comprises determining a quantitative representation of the condition or "state" of the subject's health or disease. In particular, the collection of longitudinal data over a period of time may provide a statistically significant plurality of data sets corresponding to individual samples collected over a period of time sufficient to establish a statistically significant baseline or trend of the one or more property. As used herein, the term "longitudinal" refers to data that has been acquired over a period of time and represents a plurality of data points obtained at different times over such period of time, for example, days, weeks, months, or years. Longitudinal data may include, for example, data for a variety of trends and/or patterns, including, but not limited to, cyclic structures, periodicity, changes in levels over time as indicators of changing health condition, and/or changes in variability over time as indicators of changing health condition.

In certain embodiments, a method for monitoring changes in an individual's health state over time comprises or consists essentially of: (a) detecting the presence of one or more target analytes in a first sweat sample from the subject, wherein detecting comprises: (i) collecting about 1 µL to about 50 µL of a body fluid sample comprising sweat, wherein the sample is collected using a wearable sample collection device; (ii) contacting at least a portion of the collected sample to an analyte measurement device comprising an assay unit, wherein the assay unit is configured to detect a plurality of analytes and comprises reactants for detection of the plurality of analytes, and wherein the wearable sample collection device and the analyte measurement device comprise a single integrated device; (iii) allowing the collected body fluid sample to react with the reactants, whereby a detectable reaction product is produced if a target analyte is present in the sample; and (iv) detecting the reaction product, wherein the presence of detectable reaction product indicates the presence of the target analyte in the sample. The method further comprises (b) measuring a concentration of the detected target analyte of the first sweat sample to establish a baseline level of said target analyte, wherein the amount of detectable reaction product is related to the concentration of the target analyte in the sample. Preferably, steps (a) and (b) are repeated one or more times in order to detect and measure the concentration of target analyte in a second (or third, fourth, etc.) sweat sample obtained from the individual after a predetermined interval of time. Concentrations measured for the first and second (or other) sweat samples are compared to detect a positive or negative change in the concentrations as an indicator of a positive or negative change in the individual's health state over the predetermined interval of time. Preferably, the integrated device comprising the wearable sweat collection unit and assay unit allows for frequent and/or continuous monitoring by non-invasive means. In some cases, the method can comprise determining a first "baseline" measurement of a target analyte for the subject. Subsequent measurements can be compared to the initial baseline measurement to monitor changes over time (e.g., over the course of a treatment regimen). In some cases, the method can comprise first determining a subject's personalized baseline through recurrent and/or long-term monitoring.

A target analyte is differentially present between the two samples if the amount of the target analyte in one sample is statistically significantly different from the amount of the target analyte in the other sample. As used herein, the phrase "differentially expressed" refers to differences in the quantity and/or the frequency of a target analyte present in a sample taken from patients having, for example, a particular disease as compared to a control subject.

For example, without limitation, a target analyte can be a polypeptide which is present at an elevated level or at a decreased level in sweat samples of patients having a particular condition as compared to sweat samples of control subjects. A target analyte can be differentially present in terms of quantity, frequency or both. In some cases, a target analyte is differentially present between the two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

Alternatively (or additionally), a target analyte is differentially present between the two sets of samples if the frequency of detecting the target analyte in samples of patients suffering from a particular disease or condition is statistically significantly higher or lower than in the control samples. For example, a target analyte is differentially present between the two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

In certain embodiments, decisions about therapeutic regimens for a subject (e.g., human patient) are determined according to the presence and level or concentration of one or more analytes in a collected sweat sample as described herein. Analyte data obtained using a device or method provided herein can be evaluated by a health care practitioner, e.g., manually or through use of any convenient decision tool that may include a database, algorithm, actionable interface (e.g., in the form of a graphical user interface (GUI)), outcome measure, etc. The resultant recommendation based on this evaluation step may then be employed, e.g., by a health care professional, to determine whether a particular therapeutic regimen should be modulated in some manner. For example, administration of a lower or higher dose of a medicament (e.g., higher or lower than the previously administered dosage) may be recommended based on analyte data obtained using a device or method provided herein. A determination can be communicated, e.g., by a health care practitioner, to the patient, where the determination may be in the form of an indication that no change in the therapeutic regimen should be made or that a change in the therapeutic regimen should be made. As such, the health care practitioner may inform the patient that no change in therapeutic regimen should be made and that the patient should continue to follow the therapeutic regimen as previously specified to the patient. Alternatively, the health care practitioner, following a recommendation from the evaluation step, may also forward to the patient a modified therapeutic regimen, e.g., in the form of instructions on how to change the regimen as previously specified to the patient.

The present invention has been described in terms of one or more preferred embodiments, and it should be appreciated that many equivalents, alternatives, variations, and modifications, aside from those expressly stated, are possible and within the scope of the invention. The invention will be more fully understood upon consideration of the following non-limiting Example.

Example

Sweat is a clear, hypotonic biofluid produced by eccrine and apocrine glands located in the epidermis (1, 2). Sweat is slightly acidic (pH range 4-6) and is composed mainly of water (99%), containing electrolytes (ex. Sodium, chloride, and potassium), urea, pyruvate, and lactate; but proteins, peptides, amines, amino acids, and metal ions. In smaller concentrations there are antigens, antibodies, and a variety of xenobiotics such as drugs, cosmetics, and ethanol (3). These substances are stored in sweat glands, secreted into the sweat and transported to the epidermis with partial reabsorption of sodium and chloride during transportation. This example demonstrates methods of rapid collection and analysis of sweat for the detection of analytes such as antibodies and cytokines associated with disease.

Materials and Methods

Sweat Sample Collection:

Sweat was collected from 50 healthy individuals using a Macroduct wearable sweat collection device. Participants were fitted with a Macroduct® (Elitech Group) sweat collector by first cleaning the volar region of each forearm with 70% ethanol. Macroduct® sweat collection devices were fitted to each participant's forearm as instructed by the manufacturer. We wrapped each participants forearm in clear plastic wrap to further secure the Macroduct® and improve sweat collection. Each participant was instructed to perform 30-60 minutes of moderate aerobic exercise (stationary bike, treadmill, or elliptical). Following the aerobic exercise, we removed the sweat collection devices and collected the participants sweat in a microcentrifuge tube. The sweat samples were stored at −20 degrees Celsius.

Antibody Isotyping:

Human Ig Isotyping Arrays from Ray Biotech. Each assay was performed according to the manufacturer's instructions with the following modifications. We slowly brought each slide to room temperature and added 100 µl of blocking buffer to each well. Sweat samples were diluted in blocking buffer (10 µl of sweat into 75 µl of blocking buffer). Although this Example demonstrates use of diluted sweat samples, it is to be understood that samples need not be diluted prior to analyte detection. The blocking buffer was removed from the arrays and the diluted sample was added. The slides were incubated for 16 hours on a rocking shaker at 4 degrees Celsius. The following day the slides were washed according to the instructions and the diluted biotin-conjugated anti-human Ig antibodies were added to each well, incubated for 16 hours on a rocking shaker at 4 degrees Celsius. The following day the slides were washed according to the manufacturer's instructions and the diluted strepaviden-Cy3 was added to each well and incubated for 2 hours on a rocking shaker at room temperature. Slides were washed, the gaskets were removed, the slides were dried using filtered compressed air and imaged using a Tecan Power Scanner.

Cytokine Antibody Arrays:

Human Cytokine Antibody Arrays were purchased from Ray Biotech. Each assay was performed according to the manufacturer's instructions with the following modifications. The antibody array was brought to room temperature and blocking buffer was added to each well. Sweat samples were diluted in blocking buffer (10 µl of sweat into 75 µl of blocking buffer). The blocking buffer was removed from the arrays and the diluted sample was added. The slides were incubated for 16 hours on a rocking shaker at 4 degrees Celsius. On the following day, the slides were washed according to the instructions and the diluted cocktail of biotin-conjugated Ig antibodies were added to each well, incubated for 2 hours on a rocking shaker at room temperature. The slides were washed according to the manufacturer's instructions and the diluted strepavidin-Cy3 was added to each well and incubated for 2 hours on a rocking shaker at room temperature. Slides were washed, the gaskets were removed, the slides were dried using filtered compressed air and imaged using a Tecan Power Scanner.

To normalize the signal intensity data, one sub-array was defined as a reference to which all other arrays were normalized. We calculated the normalized values using the following equation:

$$X(Ny)=X(y)*P1/P(y)$$

Where:

P1=mean signal intensity of POS spots on reference array
P(y)=mean signal intensity of POS spots on Array "y"
X(y)=mean signal intensity for spot "X" on array "y"
X(Ny)=normalized signal intensity for spot "X" on Array "y"

RAPID ELISA Assay:

Rapid Antigenic Protein In situ Display (RAPID) ELISA was performed as previously described in (4), with the following modifications. All GST fusion proteins (H1N1-HA, H1N1-NP, H3N2-HA, H3N2-NP, and EBNA) were expressed from plasmids using 1-Step Human Coupled in vitro Expression system (Thermo Scientific) at 30° C. for 1.5 hours. Following in vitro protein expression the GST-fused proteins were diluted 1:100 in 5% milk in 0.2% PBST and added to the GST coated 96 well plates at 100 µl/well and shaken at room temperature at 500 rpm for 1 hour. Plates were then washed 5 times with 0.2% PBST. During incubation the patient sweat was diluted 1:20 in 5% Milk in 0.2% PBST. Plates were then incubated with 100 µl/well diluted patient sweat, shaking at RT at 500 rpm for 16 hours at 4 degrees Celsius, and washed 5 times with 0.2% PBST. Secondary HRP conjugated goat anti-human IgG and IgA (Jackson ImmunoResearch Laboratories) to detect sweat Ab were diluted 1:10,000 in 5% milk in 0.2% PBST, and the GST positive control secondary HRP sheep anti-Mouse IgG (Jackson ImmunoResearch Laboratories) was diluted 1:6250. The secondary Abs were shaken at RT at 500 rpm for 1 hour. Plates were washed 5 times in 0.2% PBST prior to the addition of the developing buffer, Supersignal ELISA Femto Chemiluminescent Substrate (Thermo Scientific). Relative luminescence units (RLU) were measured on a Glomax 96 Microplate Luminometer (Promega, Madison, WI) using a wavelength of 425 nm. All assays were performed in duplicate, and values are plotted as mean values. RLU ratios were calculated using the RLU of a specific antigen divided by the RLU of the control GST-protein.

Results

Current point-of-care diagnostic sweat assays lack the ability to identify disease-specific antibodies from a wearable collection device. The ability to utilize sweat as a diagnostic platform can provide patients and physicians with continued monitoring of antibodies, proteins/peptides, and nucleic acids vastly improving healthcare. While, it has been previously documented that various antibody (Ig) isotypes are secreted in sweat (3), those studies required participants to collect milliliter quantities of sweat as well as requiring the researchers to perform, complicated concentration techniques to identify these antibody (Ig) isotypes. One of the key innovations in our technology is the ability to identify specific antibodies in as little as 10 µl of sweat from a FDA approved wearable sweat collection device. This provides the framework for translating these unique findings into clinical and point-of-care diagnostic assays.

Figure 1B:
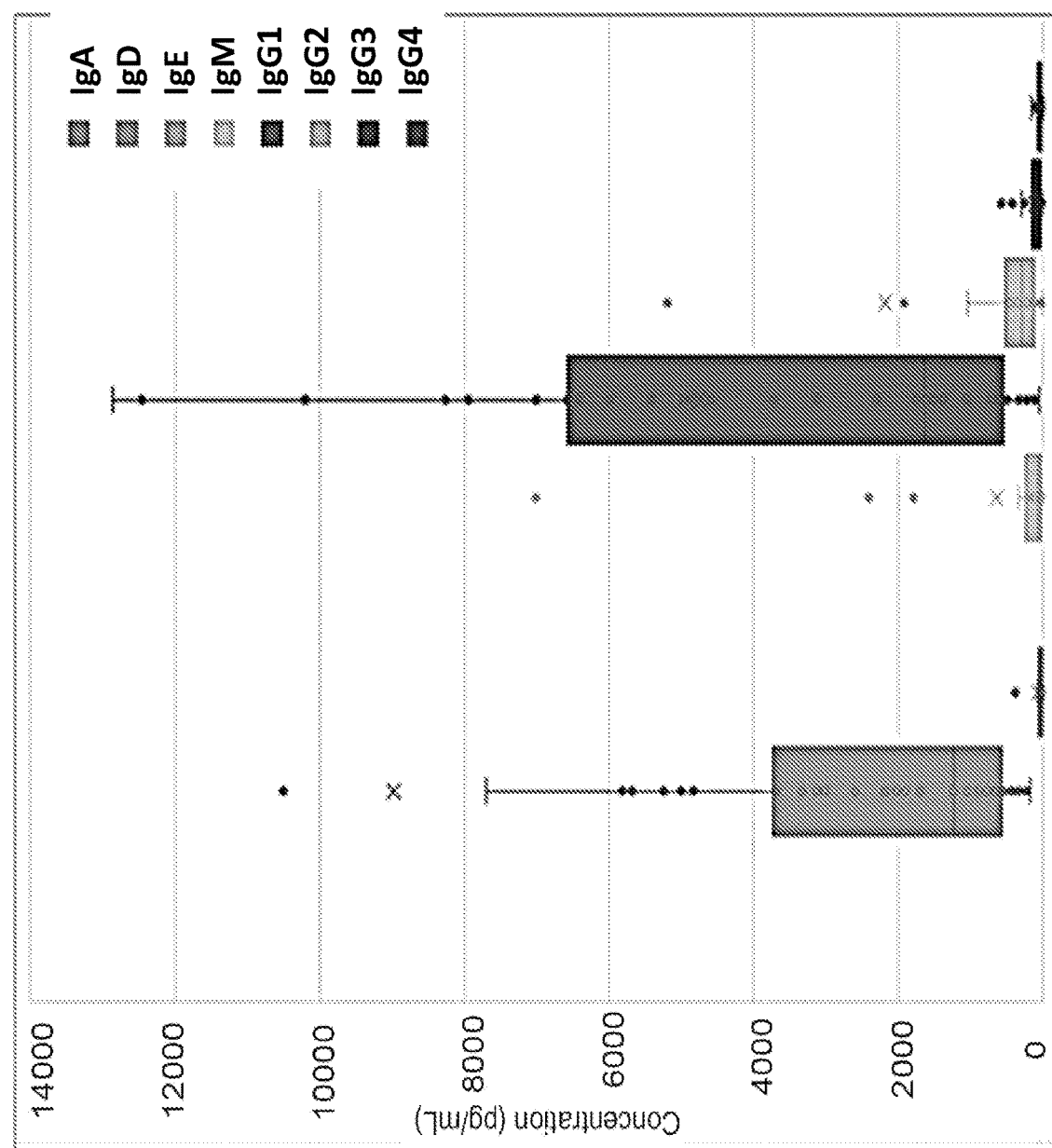

Previous studies using a small cohort of men and women identified IgA and IgE antibodies secreted in sweat. These results demonstrated vastly different concentrations among men and women as well as utilizing large volumes of concentrated sweat (2). To determine the dominant antibody (Ig) in sweat we purchased human antibody (Ig) isotyping arrays from RayBiotech containing IgG 1-4, IgA, IgD, IgE, and IgM and probed each array with 10 µl of sweat diluted in 1% BSA blocking buffer. A patient was considered positive if the average raw value was 2 standard deviations higher than the average background control (Macroduct Control, FIG. 1). For two of the antibody isotypes, IgA and IgG1, we observed significantly higher levels of these antibodies present in sweat. The levels of these two antibody isotypes were consistently high regardless of a patient's ethnicity, gender, or age (FIG. 1). For several antibody isotypes (IgD, IgE, and IgM), we observed wide variability in the concentration secreted in a patients sweat sample (FIG. 1, inset). Our results demonstrate that all antibody isotypes are secreted in eccrine sweat and that IgG and IgA specific antibodies are detectable in small volumes of sweat using an immunoassay such as, for example, a RAPID ELISA platform.

Figure 2:
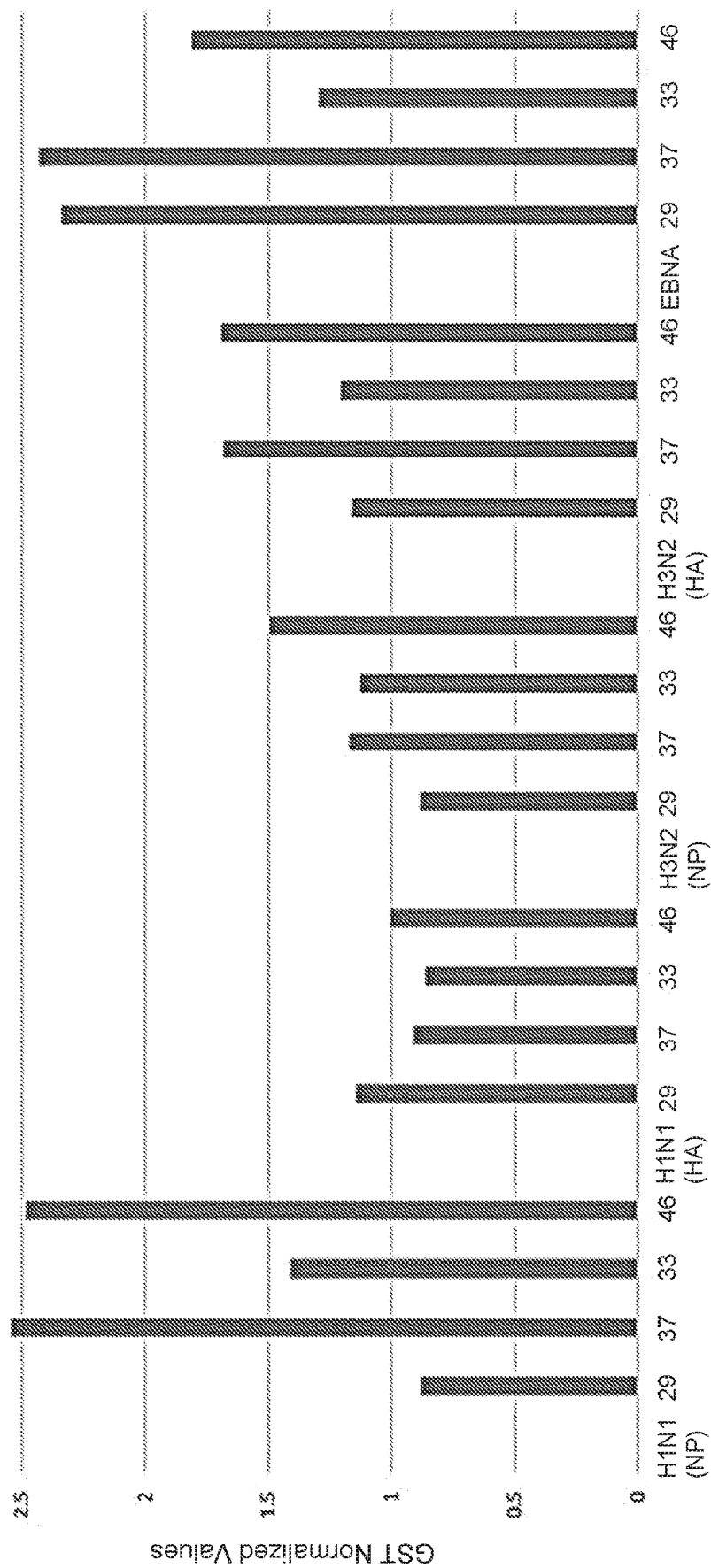
FIG. 2 is a graph of IgG influenza and EBV-specific antibodies secreted in sweat. RAPID ELISA assay was performed on sweat samples collected from four patients that received an influenza vaccine in 2016 to detect the presence of antibodies specific for influenza (H1N1 and H3N2) Nucleoprotein (NP) and Hemagglutinin (HA), as well as antibodies specific for Epstein-Barr virus protein Epstein-Barr nuclear antigen 1 (EBNA). The raw values were averaged and normalized against the GST control. A value greater than 1 indicates a positive signal.
Figures 3A, 3B:
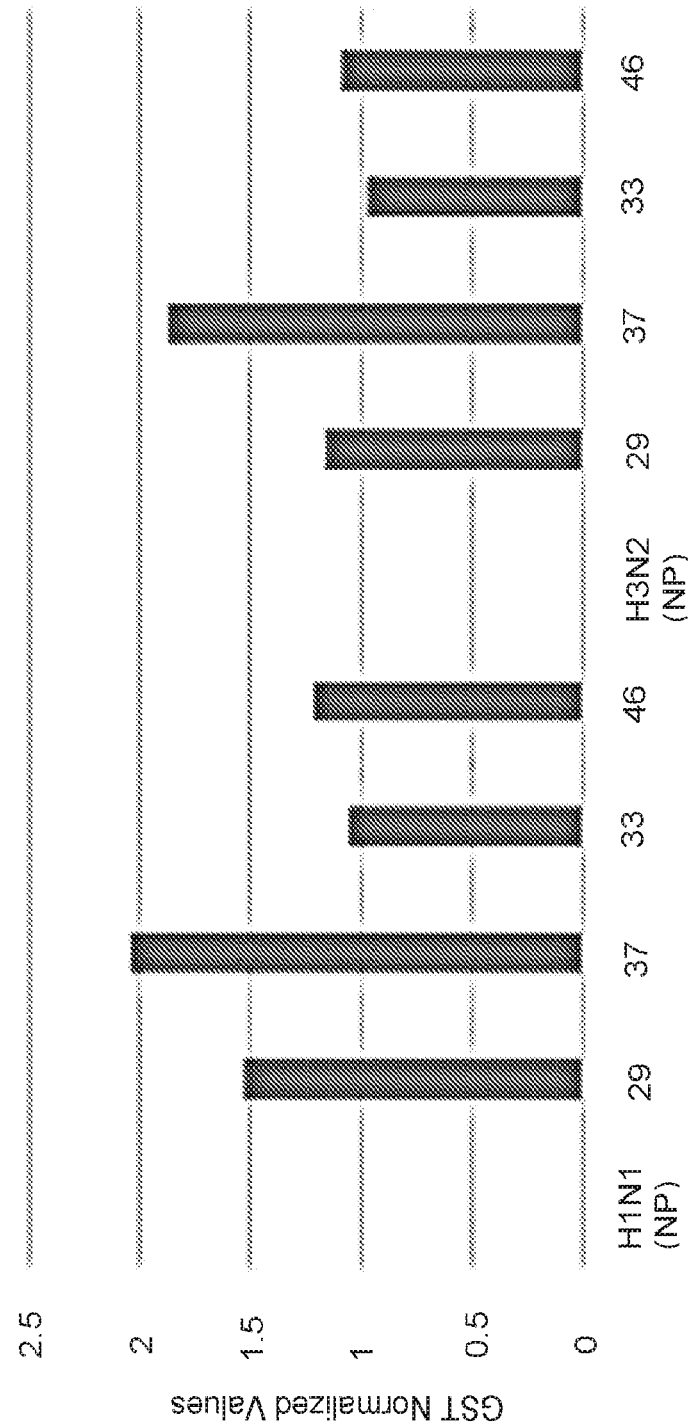
FIGS. 3A-3B demonstrate identification of IgA influenza (Flu)-specific antibodies secreted in sweat. (A) We performed a RAPID ELISA assay on 4 patients that received a received an influenza (flu) vaccine in 2016, and probed for antibodies secreted in sweat that are specific for Flu (H1N1 and H3N2) Nucleoprotein (NP). (B) We compared a patient that has never had a Flu shot (Patient 1) with a patient that had been given a Flu shot (Patient 37). In addition, we probed for antibodies specific for Epstein-Barr virus protein Epstein-Barr nuclear antigen 1 (EBNA) in a patient that was seronegative for EBNA compared to a patient was seropositive. The raw values were averaged and normalized against the GST control. A value greater than 1 indicates a positive signal.

To demonstrate the ability to detect disease specific IgG and IgA antibodies secreted in sweat, we collected small volumes (10-15 µl) of sweat from individuals that received an influenza vaccination in 2015-2016 season. The 2015-2016 influenza (flu) vaccine is directed against three different influenza strains influenza A/California/July/2009 (H1N1)pdm09, A/Switzerland/9715293/2013 (H3N2), and B/Phuket/3073/2013 (B/Yamagata lineage virus) (5). It has been previously reported that serologic viral titers are determined based on expression of antibodies specific for the HA and NP proteins (6). Therefore, we hypothesized that influenza specific IgG and IgA antibodies could be detected in sweat that are specific for HA and NP proteins. We performed a RAPID ELISA assay expressing four immunogenic proteins H1N1 HA, H1N1 NP, H3N2 HA, and H3N2 NP proteins. Four patients were screened for the presence of IgG and IgA specific antibodies by RAPID ELISA (FIG. 2). We were able to identify the presence of IgG H1N1 NP as well as H3N2 HA and NP specific antibodies secreted in sweat well above background levels. We were also able to identify IgA specific H1N1 and H3N2 NP antibodies in a select number of patients (FIGS. 3A-3B).

To further support the identification of disease specific antibodies secreted in sweat we probed the same sweat samples for the presence of IgG specific antibodies targeting Epstein-Barr Nuclear Antigen 1 (EBNA1). Epstein-Barr virus (EBV), a human herpes virus is primarily transferred by oral secretions and persists as a latent infection in human memory B-cells (7). More than 90% of adults globally are estimated to be infected with EBV and in the United States more than 80% are positive by 19 years of age (7). Although EBV is a ubiquitous pathogen, infection only manifests as symptomatic disease in a subset of individuals who harbor the virus. In its latently proliferating state, genes involved in latent viral replication, such as EBNA1 are consistently expressed. We as well as others have identified high levels of IgG specific serologic antibodies specific for EBNA1 in 80-90% of individual (4). Utilizing our RAPID ELISA assay we were able to identify IgG specific EBNA1 antibodies secreted in a small volume sweat (FIG. 1). This further demonstrates the wide applicability of sweat as a biofluid for the detection of disease specific antibodies.

In addition to antibodies, there are a variety of proteins that are secreted into the sweat that could be useful as biomarkers for the diagnosis and/or continued care of a patient. Cytokines represent a broad category of small proteins (~5-20 kDa) that are important in cell signaling, immunological responses to diseases, as well as indicating fatigue or stress. To determine if we could identify cytokines associated with stress, and indicator of disease, we collected 10-15 µl of sweat from healthy individuals after a sustained period of exercise. As a preliminary study we probed antibody arrays containing 42 unique cytokines. Using these arrays we were able to identify previously reported cytokines (e.g., IL-8, IL-6), as well as several cytokines not previously reported as detectable in sweat (FIGS. 4A-4B; Table 1 and Table 2). More importantly, we were able to demonstrate the ability to detect cytokines from a small volume of sweat using an FDA approved wearable sweat collection device. The ability to detect fluctuations in cytokine (protein) levels in sweat has broad implication in disease diagnosis and monitoring.

TABLE 1

Cytokine Data for Participant 1

| Name | Raw intensity (med) {Participant 1} | Average | St. Dev. | Normalized Values | Name | Normalized Values |
|---|---|---|---|---|---|---|
| Angiogenin | 142 | 143.5 | 2.12132 | 151.8517 | Neg | 21.46634286 |
| Angiogenin | 145 | | | | Angiogenin | 151.857206 |
| EGF | 1382 | 1262 | 169.7056 | 1335.4484 | EGF | 1335.4484 |
| EGF | 1142 | | | | ENA-78 | 104.7618 |
| ENA-78 | 95 | 99 | 5.656854 | 104.7618 | GCSF | 87.8306 |
| ENA-78 | 103 | | | | GM-CSF | 116.9311 |
| GCSF | 83 | 83 | 0 | 87.8306 | GRO | 120.6348 |
| GCSF | 83 | | | | GRO-alpha | 92.5925 |
| GM-CSF | 113 | 110.5 | 3.535534 | 116.9311 | I-309 | 38.0952 |
| GM-CSF | 108 | | | | IFN-gamma | 74.074 |
| GRO | 114 | 114 | 0 | 120.6348 | IGF-I | 122.7512 |
| GRO | 114 | | | | IL-1 alpha | 3112.6953 |
| GRO-alpha | 92 | 87.5 | 6.363961 | 92.5925 | IL-1 beta | 40.7407 |

TABLE 1-continued

Cytokine Data for Participant 1

| Name | Raw intensity (med) {Participant 1} | Average | St. Dev. | Normalized Values | Name | Normalized Values |
|---|---|---|---|---|---|---|
| GRO-alpha | 83 | | | | IL-10 | 107.4073 |
| I-309 | 36 | 36 | 0 | 38.0952 | IL-12 p70 | 95.7671 |
| I-309 | 36 | | | | IL-13 | 95.7671 |
| IFN-gamma | 71 | 70 | 1.414214 | 74.074 | IL-15 | 88.8888 |
| IFN-gamma | 69 | | | | IL-2 | 98.4126 |
| IGF-I | 119 | 116 | 4.242641 | 122.7512 | IL-3 | 116.9311 |
| IGF-I | 113 | | | | IL-4 | 42.328 |
| IL-1 alpha | 3206 | 2941.5 | 374.0595 | 3112.6953 | IL-5 | 83.5978 |
| IL-1 alpha | 2677 | | | | IL-6 | 73.5449 |
| IL-1 beta | 38 | 38.5 | 0.707107 | 40.7407 | IL-7 | 87.8306 |
| IL-1 beta | 39 | | | | IL-8 | 106.3491 |
| IL-10 | 106 | 101.5 | 6.363961 | 107.4073 | Leptin | 26.9841 |
| IL-10 | 97 | | | | MCP-1 | 128.0422 |
| IL-12 p70 | 88 | 90.5 | 3.535534 | 95.7671 | MCP-2 | 44.4444 |
| IL-12 p70 | 93 | | | | MCP-3 | 33.8624 |
| IL-13 | 90 | 90.5 | 0.707107 | 95.7671 | MCSF | 64.5502 |
| IL-13 | 91 | | | | MDC | 89.947 |
| IL-15 | 85 | 84 | 1.414214 | 88.8888 | MIG | 69.8412 |
| IL-15 | 83 | | | | MIP-1 delta | 34.3915 |
| IL-2 | 93 | 93 | 0 | 98.4126 | Oncostatin M | 61.9047 |
| IL-2 | 93 | | | | PDGF BB | 26.9841 |
| IL-3 | 114 | 110.5 | 4.949747 | 116.9311 | RANTES | 33.8624 |
| IL-3 | 107 | | | | SCF | 28.0423 |
| IL-4 | 39 | 40 | 1.414214 | 42.328 | SDF-1 | 70.3703 |
| IL-4 | 41 | | | | TARC | 88.8888 |
| IL-5 | 83 | 79 | 5.656854 | 83.5978 | TGF-beta 1 | 205.8199 |
| IL-5 | 75 | | | | Thrombopoietin | 76.7195 |
| IL-6 | 69 | 69.5 | 0.707107 | 73.5449 | TNF-alpha | 85.1851 |
| IL-6 | 70 | | | | TNF-beta | 115.3438 |
| IL-7 | 83 | 83 | 0 | 87.8306 | VEGF | 26.9841 |
| IL-7 | 83 | | | | | |
| IL-8 | 100 | 100.5 | 0.707107 | 106.3491 | | |
| IL-8 | 101 | | | | | |
| Leptin | 26 | 25.5 | 0.707107 | 26.9841 | | |
| Leptin | 25 | | | | | |
| MCP-1 | 114 | 121 | 9.899495 | 128.0422 | | |
| MCP-1 | 128 | | | | | |
| MCP-2 | 43 | 42 | 1.414214 | 44.4444 | | |
| MCP-2 | 41 | | | | | |
| MCP-3 | 32 | 32 | 0 | 33.8624 | | |
| MCP-3 | 32 | | | | | |
| MCSF | 59 | 61 | 2.828427 | 64.5502 | | |
| MCSF | 63 | | | | | |
| MDC | 85 | 85 | 0 | 89.947 | | |
| MDC | 85 | | | | | |
| MIG | 66 | 66 | 0 | 69.8412 | | |
| MIG | 66 | | | | | |
| MIP-1 delta | 32 | 32.5 | 0.707107 | 34.3915 | | |
| MIP-1 delta | 33 | | | | | |
| Neg | 20 | 20.28571 | 0.61125 | 21.46634286 | | |
| Neg | 21 | | | | | |
| Neg | 21 | | | | | |
| Neg | 21 | | | | | |
| NEG | 21 | | | | | |
| NEG | 20 | | | | | |
| NEG | 20 | | | | | |
| Neg | 19 | | | | | |
| Neg | 21 | | | | | |
| NEG | 20 | | | | | |
| NEG | 20 | | | | | |
| NEG | 20 | | | | | |
| Neg | 20 | | | | | |
| Neg | 20 | | | | | |
| Oncostatin M | 62 | 58.5 | 4.949747 | 61.9047 | | |
| Oncostatin M | 55 | | | | | |
| PDGF BB | 27 | 25.5 | 2.12132 | 26.9841 | | |
| PDGF BB | 24 | | | | | |
| Pos 1 | 11829 | 12101 | 384.6661 | | | |
| Pos 1 | 12373 | | | | | |
| Pos 2 | 9179 | 9452 | 386.0803 | | | |
| Pos 2 | 9725 | | | | | |
| Pos 3 | 4972 | 5036 | 90.50967 | | | |
| Pos 3 | 5100 | | | | | |
| RANTES | 32 | 32 | 0 | 33.8624 | | |
| RANTES | 32 | | | | | |

TABLE 1-continued

Cytokine Data for Participant 1

| Name | Raw intensity (med) {Participant 1} | Average | St. Dev. | Normalized Values | Name | Normalized Values |
|---|---|---|---|---|---|---|
| SCF | 26 | 26.5 | 0.707107 | 28.0423 | | |
| SCF | 27 | | | | | |
| SDF-1 | 68 | 66.5 | 2.12132 | 70.3703 | | |
| SDF-1 | 65 | | | | | |
| TARC | 80 | 84 | 5.656854 | 88.8888 | | |
| TARC | 88 | | | | | |
| TGF-beta 1 | 194 | 194.5 | 0.707107 | 205.8199 | | |
| TGF-beta 1 | 195 | | | | | |
| Thrombopoietin | 73 | 72.5 | 0.707107 | 76.7195 | | |
| Thrombopoietin | 72 | | | | | |
| TNF-alpha | 80 | 80.5 | 0.707107 | 85.1851 | | |
| TNF-alpha | 81 | | | | | |
| TNF-beta | 116 | 109 | 9.899495 | 115.3438 | | |
| TNF-beta | 102 | | | | | |
| VEGF | 27 | 25.5 | 2.12132 | 26.9841 | | |
| VEGF | 24 | | | | | |

TABLE 2

Cytokine Data for Participant 37

| Name | Raw intensity (med) {Participant 37} | Average | St. Dev. | Normalized Values | Name | Normalized Values |
|---|---|---|---|---|---|---|
| Angiogenin | 905 | 928.5 | 33.23401872 | #REF! | Neg | 22.222 |
| Angiogenin | 952 | | | | Angiogenin | 957.7057242 |
| EGF | 1111 | 1139 | 39.59797975 | 1175.6602 | EGF | 1175.6602 |
| EGF | 1167 | | | | ENA-78 | 93.1216 |
| ENA-78 | 88 | 91.5 | 4.949747468 | 93.1216 | GCSF | 84.656 |
| ENA-78 | 95 | | | | GM-CSF | 98.4126 |
| GCSF | 80 | 82 | 2.828427125 | 84.656 | GRO | 116.402 |
| GCSF | 84 | | | | GRO-alpha | 80.4232 |
| GM-CSF | 93 | 92.5 | 0.707106781 | 98.4126 | I-309 | 43.3862 |
| GM-CSF | 92 | | | | IFN-gamma | 69.8412 |
| GRO | 110 | 112.5 | 3.535533906 | 116.402 | IGF-I | 116.402 |
| GRO | 115 | | | | IL-1 alpha | 6728.0356 |
| GRO-alpha | 76 | 76.5 | 0.707106781 | 80.4232 | IL-1 beta | 55.0264 |
| GRO-alpha | 77 | | | | IL-10 | 98.4126 |
| I-309 | 41 | 37 | 5.656854249 | 43.3862 | IL-12 p70 | 89.947 |
| I-309 | 33 | | | | IL-13 | 94.1798 |
| IFN-gamma | 66 | 67.5 | 2.121320344 | 69.8412 | IL-15 | 79.365 |
| IFN-gamma | 69 | | | | IL-2 | 85.7142 |
| IGF-I | 110 | 114 | 5.656854249 | 116.402 | IL-3 | 120.6348 |
| IGF-I | 118 | | | | IL-4 | 41.2698 |
| IL-1 alpha | 6358 | 5833.5 | 741.7550135 | 6728.0356 | IL-5 | 78.3068 |
| IL-1 alpha | 5309 | | | | IL-6 | 71.9576 |
| IL-1 beta | 52 | 51.5 | 0.707106781 | 55.0264 | IL-7 | 86.7724 |
| IL-1 beta | 51 | | | | IL-8 | 94.1798 |
| IL-10 | 93 | 87.5 | 7.778174593 | 98.4126 | Leptin | 39.1534 |
| IL-10 | 82 | | | | MCP-1 | 141.7988 |
| IL-12 p70 | 85 | 87.5 | 3.535533906 | 89.947 | MCP-2 | 45.5026 |
| IL-12 p70 | 90 | | | | MCP-3 | 33.8624 |
| IL-13 | 89 | 87 | 2.828427125 | 94.1798 | MCSF | 78.3068 |
| IL-13 | 85 | | | | MDC | 96.2962 |
| IL-15 | 75 | 80 | 7.071067812 | 79.365 | MIG | 62.4338 |
| IL-15 | 85 | | | | MIP-1 delta | 31.746 |
| IL-2 | 81 | 80.5 | 0.707106781 | 85.7142 | Oncostatin M | 62.4338 |
| IL-2 | 80 | | | | PDGF BB | 47.619 |
| IL-3 | 114 | 112.5 | 2.121320344 | 120.6348 | RANTES | 30.6878 |
| IL-3 | 111 | | | | SCF | 29.6296 |
| IL-4 | 39 | 38.5 | 0.707106781 | 41.2698 | SDF-1 | 63.492 |
| IL-4 | 38 | | | | TARC | 85.7142 |
| IL-5 | 74 | 73.5 | 0.707106781 | 78.3068 | TGF-beta 1 | 165.0792 |
| IL-5 | 73 | | | | Thrombopoietin | 77.2486 |
| IL-6 | 68 | 66.5 | 2.121320344 | 71.9576 | TNF-alpha | 78.3068 |
| IL-6 | 65 | | | | TNF-beta | 120.6348 |
| IL-7 | 82 | 79 | 4.242640687 | 86.7724 | VEGF | 42.328 |
| IL-7 | 76 | | | | | |
| IL-8 | 89 | 97.5 | 12.02081528 | 94.1798 | | |
| IL-8 | 106 | | | | | |
| Leptin | 37 | 39 | 2.828427125 | 39.1534 | | |
| Leptin | 41 | | | | | |

TABLE 2-continued

Cytokine Data for Participant 37

| Name | Raw intensity (med) {Participant 37} | Average | St. Dev. | Normalized Values | Name | Normalized Values |
|---|---|---|---|---|---|---|
| MCP-1 | 134 | 135 | 1.414213562 | 141.7988 | | |
| MCP-1 | 136 | | | | | |
| MCP-2 | 43 | 43 | 0 | 45.5026 | | |
| MCP-2 | 43 | | | | | |
| MCP-3 | 32 | 31.5 | 0.707106781 | 33.8624 | | |
| MCP-3 | 31 | | | | | |
| MCSF | 74 | 74 | 0 | 78.3068 | | |
| MCSF | 74 | | | | | |
| MDC | 91 | 90.5 | 0.707106781 | 96.2962 | | |
| MDC | 90 | | | | | |
| MIG | 59 | 57 | 2.828427125 | 62.4338 | | |
| MIG | 55 | | | | | |
| MIP-1 delta | 30 | 30.5 | 0.707106781 | 31.746 | | |
| MIP-1 delta | 31 | | | | | |
| Neg | 21 | 20.92857143 | 0.474631147 | 22.2222 | | |
| Neg | 21 | | | | | |
| Neg | 21 | | | | | |
| Neg | 22 | | | | | |
| NEG | 20 | | | | | |
| NEG | 21 | | | | | |
| NEG | 21 | | | | | |
| Neg | 20 | | | | | |
| Neg | 21 | | | | | |
| NEG | 21 | | | | | |
| NEG | 21 | | | | | |
| NEG | 21 | | | | | |
| Neg | 21 | | | | | |
| Neg | 21 | | | | | |
| Oncostatin M | 59 | 57.5 | 2.121320344 | 62.4338 | | |
| Oncostatin M | 56 | | | | | |
| PDGF BB | 45 | 47.5 | 3.535533906 | 47.619 | | |
| PDGF BB | 50 | | | | | |
| Pos 1 | 14224 | 12993.5 | 1740.189789 | | | |
| Pos 1 | 11763 | | | | | |
| Pos 2 | 9933 | 10062 | 182.4335495 | | | |
| Pos 2 | 10191 | | | | | |
| Pos 3 | 4817 | 4830 | 18.38477631 | | | |
| Pos 3 | 4843 | | | | | |
| RANTES | 29 | 29.5 | 0.707106781 | 30.6878 | | |
| RANTES | 30 | | | | | |
| SCF | 28 | 27.5 | 0.707106781 | 29.6296 | | |
| SCF | 27 | | | | | |
| SDF-1 | 60 | 55.5 | 6.363961031 | 63.492 | | |
| SDF-1 | 51 | | | | | |
| TARC | 81 | 81 | 0 | 85.7142 | | |
| TARC | 81 | | | | | |
| TGF-beta 1 | 156 | 153 | 4.242640687 | 165.0792 | | |
| TGF-beta 1 | 150 | | | | | |
| Thrombopoietin | 73 | 75 | 2.828427125 | 77.2486 | | |
| Thrombopoietin | 77 | | | | | |
| TNF-alpha | 74 | 75 | 1.414213562 | 78.3068 | | |
| TNF-alpha | 76 | | | | | |
| TNF-beta | 114 | 70 | 62.22539674 | 120.6348 | | |
| TNF-beta | 26 | | | | | |
| VEGF | 40 | 43 | 4.242640687 | 42.328 | | |
| VEGF | 46 | | | | | |

REFERENCES

1. Sato K, Kang W H, Saga K, Sato K T. Biology of sweat glands and their disorders. II. Disorders of sweat gland function. Journal of the American Academy of Dermatology. 1989; 20(5 Pt 1):713-26. PubMed PMID: 2654213.
2. Sato K, Kang W H, Saga K, Sato K T. Biology of sweat glands and their disorders. I. Normal sweat gland function. Journal of the American Academy of Dermatology. 1989; 20(4):537-63. PubMed PMID: 2654204.
3. Jadoon S, Karim S, Akram M R, Kalsoom Khan A, Zia M A, Siddiqi A R, Murtaza G. Recent developments in sweat analysis and its applications. International journal of analytical chemistry. 2015; 2015:164974. doi: 10.1155/2015/164974. PubMed PMID: 25838824; PubMed Central PMCID: PMC4369929.
4. Wong J, Sibani S, Lokko N N, LaBaer J, Anderson K S. Rapid detection of antibodies in sera using multiplexed self-assembling bead arrays. Journal of immunological methods. 2009; 350(1-2):171-82. doi: 10.1016/j.jim.2009.08.013. PubMed PMID: 19732778; PubMed Central PMCID: PMC2974181.
5. Komissarov A, Fadeev A, Petrov S, Sergeeva M, Sintsova K, Egorova A, Pisareva M, Buzitskaya Z, Musaeva T, Danilenko D, Konovalova N, Petrova P, Stolyarov K, Smorodintseva E, Burtseva E, Krasnoslobodtsev K, Kirillova E, Karpova L, Eropkin M, Sominina A, Grudinin M. Rapid spread of influenza A(H1N1)pdm09 viruses with a new set of specific mutations in the internal genes in the beginning of 2015/2016 epidemic season in Moscow and Saint-Petersburg (Russian Federation). Influenza and other respiratory viruses. 2016. doi: 10.1111/irv. 12389. PubMed PMID: 26992820.

6. Petrie J G, Ohmit S E, Johnson E, Truscon R, Monto A S. Persistence of Antibodies to Influenza Hemagglutinin and Neuraminidase Following One or Two Years of Influenza Vaccination. The Journal of infectious diseases. 2015; 212(12): 1914-22. doi: 10.1093/infdis/jiv313. PubMed PMID: 26014800; PubMed Central PMCID: PMC4655854.

7. Coghill A E, Hildesheim A. Epstein-Barr virus antibodies and the risk of associated malignancies: review of the literature. American journal of epidemiology. 2014; 180 (7):687-95. doi: 10.1093/aje/kwu176. PubMed PMID: 25167864; PubMed Central PMCID: PMC4271109.

We claim:

1. A method for determining a concentration of a target analyte in sweat, comprising the steps of:
   providing between about 1 μL and about 50 μL of a body fluid sample comprising sweat, wherein the sample is collected using a wearable sample collection device worn by a subject while the subject is performing aerobic exercise;
   contacting at least a portion of the collected sample to an analyte measurement device comprising an assay unit, wherein the assay unit is configured to detect a plurality of analytes selected from the group consisting of disease-associated IgG antibodies and disease-associated IgA antibodies, and wherein the assay unit comprises reactants for detection of the plurality of analytes;
   allowing the collected body fluid sample to react with the reactants, whereby a detectable reaction product is produced if the target analyte is present in the sample; and
   detecting and measuring the reaction product, wherein the presence of detectable reaction product indicates the presence of the target analyte in the sample; and wherein the amount of detectable reaction product is related to the concentration of the target analyte in the sample.

2. The method of claim 1, wherein the target analyte is an antibody against an antigen selected from the group consisting of Epstein Barr Virus nuclear antigen 1 (EBNA1), H1N1 influenza HA, H1N1 influenza NP, H3N2 influenza HA, and H3N2 influenza NP.

3. The method of claim 1, wherein the reactants comprise a capture probe that binds to the target analyte, and wherein the presence of a detectable reaction product indicates the binding of the capture probe to the target analyte.

4. The method of claim 3, wherein the capture probe comprises a detectable moiety.

5. The method of claim 1, wherein the assay unit is configured to run an enzymatic assay yielding a colored product, is configured to run an immunoassay, or both.

6. The method of claim 1, wherein the reactants are selected from the group of enzymes, substrates, colorimetric indicators, antibodies, and combinations thereof.

7. The method of claim 1, wherein the body fluid sample consists essentially of sweat.

8. A method of monitoring changes in an subject's health state over time, the method comprising
   (a) detecting the presence of one or more target analytes in a first sweat sample from the subject, wherein detecting comprises:
      (i) collecting between about 5 μL to about 20 μL of a body fluid sample comprising sweat, wherein the sample is collected using a wearable sample collection device worn by the subject while the subject is performing aerobic exercise;
      (ii) contacting at least a portion of the collected sample to an analyte measurement device comprising an assay unit, wherein the assay unit is configured to detect a plurality of analytes selected from the group consisting of disease-associated IgG antibodies and disease-associated IgA antibodies, and wherein the assay unit comprises reactants for detection of the plurality of analytes;
      (iii) allowing the collected body fluid sample to react with the reactants, whereby a detectable reaction product is produced if a target analyte is present in the sample; and
      (iv) detecting the reaction product, wherein the presence of detectable reaction product indicates the presence of the target analyte in the sample;
   (b) measuring a concentration of the detected target analyte of the first sweat sample to establish a baseline level of said target analyte, wherein the amount of detectable reaction product is related to the concentration of the target analyte in the sample;
   (c) repeating steps (a) and (b) to detect and measure the concentration of target analyte in a second sweat sample obtained from the individual at after a predetermined interval of time;
   (d) comparing the concentrations measured for the first and second sweat samples to detect a positive or negative change in the concentrations as an indicator of a positive or negative change in the individual's health state over the predetermined interval of time.

9. The method of claim 8, wherein the target analyte is an antibody against an antigen selected from the group consisting of Epstein Barr Virus nuclear antigen 1 (EBNA1), H1N1 influenza HA, H1N1 influenza NP, H3N2 influenza HA, and H3N2 influenza NP.

10. The method of claim 8, wherein each of the first and second sweat samples consists essentially of sweat.

11. The method of claim 8, wherein the wearable collection device is positioned at essentially the same location on the individual's body for each sample collection step.

12. The method of claim 8, wherein the reactants comprise a capture probe that binds to the target analyte, and wherein the presence of a detectable reaction product indicates the binding of the capture probe to the target analyte.

13. The method of claim 8, wherein the assay unit is configured to run an enzymatic assay yielding a colored product, is configured to run an immunoassay, or both.

14. The method of claim 8, wherein the reactants are selected from the group of enzymes, substrates, colorimetric indicators, antibodies, and combinations thereof.

15. A method of detecting a target disease-specific antibody in a body fluid sample, the method comprising:
   (a) collecting between about 5 μL to about 20 μL of the body fluid sample comprising sweat, wherein the sample is collected using a wearable sample collection device worn by a subject while the subject is performing exercise;
   (b) contacting at least a portion of the collected sample to an analyte measurement device comprising an assay unit, wherein the assay unit is configured to detect at least one disease-specific antibody, wherein the disease-specific antibody is an IgG antibody or an IgA antibody, and wherein the assay unit comprises reactants for detection of the at least one disease-specific antibody;

(c) allowing the collected body fluid sample to react with the reactants, whereby a detectable reaction product is produced if the target disease-specific antibody is present in the sample; and (d) detecting and measuring the reaction product, wherein the presence of detectable reaction product indicates the presence of the target disease-specific antibody in the sample; and wherein the amount of detectable reaction product is related to the concentration of the target disease-specific antibody in the sample.

16. The method of claim 15, wherein the target disease specific antibody is against an antigen selected from the group consisting of Epstein Barr Virus (EBV), H1N1 influenza HA, H1N1 influenza NP, H3N2 influenza HA, and H3N2 influenza NP.

17. The method of claim 15, further comprising: (e) employing the concentration determined in (d) to distinguish between healthy subjects and subjects having a target analyte-associated disease.

18. The method of claim 15, wherein the body fluid sample consists essentially of sweat.

* * * * *

UNITED STATES PATENT AND TRADEMARK OFFICE
CERTIFICATE OF CORRECTION

| | |
|---|---|
| PATENT NO. | : 11,832,801 B2 |
| APPLICATION NO. | : 16/317326 |
| DATED | : December 5, 2023 |
| INVENTOR(S) | : Benjamin Katchman et al. |

It is certified that error appears in the above-identified patent and that said Letters Patent is hereby corrected as shown below:

On the Title Page

Item (71) Applicant:, "cARIZONA BOARD OF REGENTS ON BEHALF OF ARIZONA STATE UNIVERSITY" should be --"ARIZONA BOARD OF REGENTS ON BEHALF OF ARIZONA STATE UNIVERSITY--.

Signed and Sealed this
Twentieth Day of February, 2024

Katherine Kelly Vidal
*Director of the United States Patent and Trademark Office*